US009139827B2

(12) United States Patent
Mirkin et al.

(10) Patent No.: US 9,139,827 B2
(45) Date of Patent: Sep. 22, 2015

(54) POLYVALENT RNA-NANOPARTICLE COMPOSITIONS

(75) Inventors: Chad A. Mirkin, Wilmette, IL (US); David A. Giljohann, Chicago, IL (US); Dwight Seferos, Evanston, IL (US); Andrew E. Prigodich, Evanston, IL (US); Pinal C. Patel, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 367 days.

(21) Appl. No.: 12/625,537

(22) Filed: Nov. 24, 2009

(65) Prior Publication Data

US 2010/0136682 A1    Jun. 3, 2010

Related U.S. Application Data

(60) Provisional application No. 61/117,449, filed on Nov. 24, 2008.

(51) Int. Cl.
| | | |
|---|---|---|
| *C07H 21/04* | (2006.01) | |
| *C12N 15/11* | (2006.01) | |
| *A61K 47/48* | (2006.01) | |
| *A61K 48/00* | (2006.01) | |

(52) U.S. Cl.
CPC ........ *C12N 15/111* (2013.01); *A61K 47/48861* (2013.01); *A61K 48/00* (2013.01); *C12N 2310/14* (2013.01); *C12N 2310/351* (2013.01); *C12N 2320/32* (2013.01)

(58) Field of Classification Search
CPC ........... A61K 47/48861; C12N 15/111; C12N 2310/14
See application file for complete search history.

(56) References Cited

U.S. PATENT DOCUMENTS

| | | |
|---|---|---|
| 3,687,808 A | 8/1972 | Merigan et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |

(Continued)

FOREIGN PATENT DOCUMENTS

| | | |
|---|---|---|
| EP | 1072679 A2 | 1/2001 |
| EP | 1674128 A1 | 6/2006 |

(Continued)

OTHER PUBLICATIONS

Allara et al., Spontaneously organized molecular assemblies. 1. Formation, dynamics, and physical properties of n-Alkanoic acids adsorbed from solution on an oxidized aluminum surface, *Langmuir*, 1:45-52 (1985).
Altschul et al., Basic local alignment search tool, *J. Mol. Biol.*, 215:403-10 (1990).
Burwell, Modified silica gels as adsorbents and catalysts, *Chem. Tech.*, 4, 370-7 (1974).
Cook, Medicinal chemistry of antisense oligonucleotides—future opportunities, *Anti-Cancer Drug Design*, 6:585-607 (1991).
Demers et al., A fluorescence-based method for determining the surface coverage and hybridization efficiency of thiol-capped oligonucleotides bound to gold thin films and nanoparticles, *Anal. Chem.*, 72: 5535 (2000).
DeMesmaeker et al., Backbone modifications in oligonucleotides and peptide nucleic acid systems, *Curr. Opin. Structural Biol.*, 5:343-55 (1995).
Elghanian et al., Selective colorimetric detection of polynucleotides based on the distance-dependent optical properties of gold nanoparticles, *Science*, 277: 1078-81 (1997).

(Continued)

*Primary Examiner* — Jon E Angell
(74) *Attorney, Agent, or Firm* — Marshall, Gerstein & Borun LLP

(57) ABSTRACT

The present invention concerns nanoparticles functionalized with duplex RNA for a variety of uses, including but not limited to gene regulation. More specifically, the disclosure provides a new strategy for conjugating RNA to a nanoparticle to achieve increased stability and activity.

24 Claims, 8 Drawing Sheets

(56) References Cited

U.S. PATENT DOCUMENTS

| | | |
|---|---|---|
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,544,776 B1 | 4/2003 | Gold et al. |
| 6,582,921 B2 | 6/2003 | Mirkin et al. |
| 6,602,669 B2 | 8/2003 | Letsinger et al. |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,678,548 B1 | 1/2004 | Echauz et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,806,289 B1 | 10/2004 | Lippard et al. |

(56) References Cited

U.S. PATENT DOCUMENTS

| | | |
|---|---|---|
| 6,812,334 B1 | 11/2004 | Mirkin et al. |
| 6,818,753 B2 | 11/2004 | Mirkin et al. |
| 6,827,979 B2 | 12/2004 | Mirkin et al. |
| 6,828,432 B2 | 12/2004 | Mirkin et al. |
| 6,844,161 B2 | 1/2005 | Siani et al. |
| 6,861,221 B2 | 3/2005 | Mirkin et al. |
| 6,878,814 B2 | 4/2005 | Mirkin et al. |
| 6,974,669 B2 | 12/2005 | Mirkin et al. |
| 6,991,900 B2 | 1/2006 | Shizuya |
| 7,098,320 B1 | 8/2006 | Mirkin et al. |
| 7,138,520 B2 | 11/2006 | Lippard et al. |
| 7,223,833 B1 | 5/2007 | Nielsen et al. |
| 7,238,472 B2 | 7/2007 | Mirkin et al. |
| 7,323,309 B2 | 1/2008 | Mirkin et al. |
| 7,332,586 B2 | 2/2008 | Franzen et al. |
| 7,611,728 B2 | 11/2009 | Kidane et al. |
| 7,638,557 B2 | 12/2009 | Lipkin et al. |
| 7,651,979 B2 | 1/2010 | Lippard et al. |
| 7,667,004 B2 | 2/2010 | Zhong et al. |
| 7,727,969 B2 | 6/2010 | Farokhzad et al. |
| 8,252,756 B2 | 8/2012 | Mirkin et al. |
| 2002/0172953 A1 | 11/2002 | Mirkin et al. |
| 2003/0147966 A1 | 8/2003 | Franzen et al. |
| 2003/0181412 A1 | 9/2003 | Erikson |
| 2004/0147022 A1* | 7/2004 | Baker et al. ............ 435/375 |
| 2004/0219565 A1 | 11/2004 | Kauppinen et al. |
| 2004/0247680 A1 | 12/2004 | Farokhzad et al. |
| 2004/0248099 A1 | 12/2004 | Goppelt et al. |
| 2005/0059016 A1 | 3/2005 | Ecker et al. |
| 2005/0074753 A1 | 4/2005 | Goldsborough |
| 2005/0096263 A1 | 5/2005 | Keay et al. |
| 2005/0197315 A1 | 9/2005 | Taira et al. |
| 2005/0214782 A1 | 9/2005 | Chen et al. |
| 2005/0244858 A1* | 11/2005 | Rossi et al. ............ 435/6 |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0105343 A1 | 5/2006 | Zetter et al. |
| 2006/0159921 A1 | 7/2006 | Murthy et al. |
| 2006/0183247 A1 | 8/2006 | Kim et al. |
| 2006/0188560 A1 | 8/2006 | Cheresh et al. |
| 2006/0233712 A1 | 10/2006 | Penades et al. |
| 2006/0252037 A1 | 11/2006 | Kolesnick et al. |
| 2006/0275371 A1 | 12/2006 | Dai et al. |
| 2007/0105139 A1 | 5/2007 | Nishigaki et al. |
| 2008/0057128 A1 | 3/2008 | Li et al. |
| 2008/0194463 A1 | 8/2008 | Weller et al. |
| 2008/0213177 A1 | 9/2008 | Rademacher et al. |
| 2008/0220072 A1 | 9/2008 | Unger et al. |
| 2008/0279946 A1 | 11/2008 | Hainfeld |
| 2008/0305106 A1 | 12/2008 | Brennan et al. |
| 2008/0306016 A1 | 12/2008 | Mirkin et al. |
| 2008/0317749 A1 | 12/2008 | Kastelein et al. |
| 2008/0317768 A1 | 12/2008 | Bianchi |
| 2009/0035576 A1 | 2/2009 | Prasad et al. |
| 2009/0081244 A1 | 3/2009 | Glenn et al. |
| 2009/0148384 A1 | 6/2009 | Fischer et al. |
| 2009/0155173 A1 | 6/2009 | Scherman et al. |
| 2009/0209629 A1 | 8/2009 | Mirkin et al. |
| 2009/0286853 A1 | 11/2009 | Gryaznov et al. |
| 2010/0167051 A1 | 7/2010 | Goia et al. |
| 2010/0183504 A1 | 7/2010 | Chen |
| 2010/0183634 A1 | 7/2010 | Luo et al. |
| 2011/0172404 A1 | 7/2011 | Luo et al. |
| 2011/0262976 A1 | 10/2011 | Kandula et al. |
| 2013/0123333 A1 | 5/2013 | Mirkin et al. |

FOREIGN PATENT DOCUMENTS

| | | |
|---|---|---|
| WO | WO-89/02439 | 3/1989 |
| WO | WO-93/07883 A1 | 4/1993 |
| WO | WO-93/21259 | 10/1993 |
| WO | WO-95/06731 | 3/1995 |
| WO | WO-95/11910 | 5/1995 |
| WO | WO-97/12896 A1 | 4/1997 |
| WO | WO-98/04740 | 2/1998 |
| WO | WO-98/04740 A1 | 2/1998 |
| WO | WO-98/39352 A1 | 9/1998 |
| WO | WO-98/47343 | 10/1998 |
| WO | WO-99/11655 | 3/1999 |
| WO | WO-99/14226 A2 | 3/1999 |
| WO | WO-00/43045 A1 | 7/2000 |
| WO | WO-01/00876 A1 | 1/2001 |
| WO | WO-01/49869 A1 | 7/2001 |
| WO | WO-01/51665 A2 | 7/2001 |
| WO | WO-01/73123 A2 | 10/2001 |
| WO | WO-02/44321 A2 | 6/2002 |
| WO | WO-02/096262 A2 | 12/2002 |
| WO | WO-03/008539 A2 | 1/2003 |
| WO | WO-03/051278 A2 | 6/2003 |
| WO | WO-2005/116226 A2 | 12/2005 |
| WO | WO-2006/012695 A1 | 2/2006 |
| WO | WO-2006/045541 A1 | 5/2006 |
| WO | WO-2006/064451 | 6/2006 |
| WO | WO-2006/064453 | 6/2006 |
| WO | WO-2006/138145 A1 | 12/2006 |
| WO | WO-2007/047455 | 4/2007 |
| WO | WO-2008/098248 | 8/2008 |
| WO | WO-2008/141289 A1 | 11/2008 |
| WO | WO-2008/151049 A2 | 12/2008 |
| WO | WO-2010/060110 A1 | 5/2010 |
| WO | WO-2010/081049 | 7/2010 |
| WO | WO-2010/120420 | 10/2010 |
| WO | WO-2011/017690 | 2/2011 |

OTHER PUBLICATIONS

Eltekova et al., Adsorption of aromatic compounds from solutions on titanium dioxide and silica, *Langmuir*, 3:951-7 (1987).

Englisch et al., Chemically modified oligonucleotides as probes and inhibitors, *Angew. Chem. Int. Ed. English*, 30:613-29 (1991).

Enustun et al., Coagulation of colloidal gold, *J. Am. Chem. Soc.*, 85: 3317-28 (1963).

Faulds et al., Evaluation of surface-enhanced resonance Raman scattering for quantitative DNA analysis, *Anal. Chem.*, 76: 412-7 (2004).

Freier et al., The ups and downs of nucleic acid duplex stability: structure-stability studies on chemically-modified DNA:RNA duplexes, *Nucleic Acids Res.*, 25:4429-43 (1997).

Frens, Controlled nucleation for the regulation of the particle size in monodisperse gold suspensions, *Nature Physical Science*, 241:20-2 (1973).

Gestwicki et al., Influencing receptor-ligand binding mechanisms with multivalent ligand architecture, *J. Am. Chem. Soc.*, 124: 14922-33 (2002).

Gilojohann et al., Oligonucleotide loading determines cellular uptake of DNA-modified gold nanoparticles, *Nano Lett.*, 7:3818 (2007).

Grabar et al., Preparation and characterization of Au colloid monolayers, *Anal. Chem.*, 67, 735-43 (1995).

Hamilton et al., A species of small antisense RNA in post-transcriptional gene silencing in plants, *Science*, 286: 950-2 (1999).

Hammond et al., An RNA-directed nuclease mediates post-transcriptional gene silencing in *Drosophila* cells, *Nature*, 404: 293-296 (2000).

Hayashi, Ultrafine particles, *J. Vac. Sci. Technol.*, A5(4) :1375-84 (1987).

Hayashi, Ultrafine particles, *Physics Today*, 44-60 (Dec. 1987).

Hickman et al., Combining spontaneous molecular assembly with microfabrication to pattern surfaces: selective binding of isonitriles to platinum microwires and characterization by electrochemistry and surface spectroscopy, *J. Am. Chem. Soc.*, 111:7271-2 (1989).

Hubbard, Electrochemistry of well-defined surfaces, *Acc. Chem. Res.*, 13:177-84 (1980).

Hurst et al., Maximizing DNA loading on a range of gold nanoparticle sizes, *Anal. Chem.*, 78:8313 (2006).

Iler, *The Chemistry of Silica*, Chapter 6, New York: John Wiley & Sons (1979).

Jin et al., What controls the melting properties of DNA-linked gold nanoparticle assemblies?, *J. Am. Chem. Soc.*, 125: 1643 (2003).

(56) References Cited

OTHER PUBLICATIONS

Katz, The reversible reaction of sodium thymonucleate and mercuric chloride, *J. Am. Chem. Soc.*, 74:2238-45 (1952).
Kosturko et al., The crystal and molecular structure of a 2:1 complex of 1-methylthymine-mercury(II), *Biochem.*, 13:3949-52 (1974).
Lee et al., Adsorption of ordered zirconium phophonate multilayer films on silicon and gold surfaces, *J. Phys. Chem.*, 92:2597-601 (1988).
Liu et al., Accelerated color change of gold nanoparticles assembled by DNAzymes for simple and fast colorimetric Pb2+ detection, *J. Am. Chem. Soc.* 126: 12298-305 (2004).
Liu et al., Argonaute2 is the catalytic engine of mammalian RNAi, *Science*, 305(5689): 1437-41 (2004).
Lytton-Jean et al., A thermodynamic investigation into the binding properties of DNA functionalized gold nanoparticle probes and molecular fluorophore probes, *J. Am. Chem Soc.*, 127: 12754-5 (2005).
Maoz et al., Penetration-controlled reactions in organized monolayer assemblies. 1. Aqueous permanganate interaction with monolayer and multilayer films of long-chain surfactants, *Langmuir*, 3:1034-44 (1987).
Maoz et al., Penetration-controlled reactions in organized monolayer assemblies. 2. Aqueous permanganate interaction with self-assembling monolayers of long-chain surfactants, *Langmuir*, 3:1045-51 (1987).
Marinakos et al., Gold nanoparticles as templates for the synthesis of hollow nanometer-sized conductive polymer capsules, *Adv. Mater.*, 11:34-37 (1999).
Marinakos et al., Template synthesis of one-dimensional Au, Au-poly(pyrrole), and poly(pyrrole) nanoparticle arrays, *Chem. Mater.*, 10: 1214-19 (1998).
Martin et al., 38. Ein neuer zugang zu 2'-O-alkylribonucleosiden and eigenschaften deren oligonucleotide, *Helv. Chim. Acta*, 78:486-504 (1995) [English abstract only.].
Matteucci et al., Synthesis of deoxyoligonucleotides on a polymer support, *J. Am. Chem. Soc.*, 103, 3185-91 (1981).
Mirkin et al., A DNA-based method for rationally assembling nanoparticles into macroscopic materials, *Nature*, 382: 607 (1996).
*MRS Bulletin, Fine Particles Pt. II*, pp. 16-47 (Jan. 1990).
Mucic et al., Synthesis and characterization of DNA with ferrocenyl groups attached to their 5'-termini: electrochemical characterization of a redox-active nucleotide monolayer, *Chem. Commun.*, 555-7 (1996).
Nam et al., Nanoparticle-based bio-bar codes for the ultrasensitive detection of proteins, *Science*, 301: 1884-6 (2003).
Nielsen et al., Sequence-selective recognition of DNA by strand displacement with a thymine-substituted polyamide, *Science*, 254:1497-500 (1991).
Nuzzo et al., Spontaneously organized molecular assemblies. 3. Preparation and properties of solution adsorbed monolayers of organic disulfides on gold surfaces, *J. Am. Chem. Soc.*, 109:2358-68 (1987).
Nykypanchuk et al., DNA-guided crystallization of colloidal nanoparticles, *Nature*, 451:549-52 (2008).
Park et al., DNA-programmable nanoparticle crystallization, *Nature*, 451: 553-6 (2008).
Parrish et al., Functional anatomy of a dsRNA trigger: differential requirement for the two trigger strands in RNA interference, *Mol. Cell*, 6: 1077-87 (2000).
Sanghvi et al., Heterocyclic base modifications in nucleic acids and their applications in antisense oligonucleotides, Chapter 15 In: Crooke et al. (eds.), *Antisense Research and Applications*, Boca Raton: CRC Press (1993).
Sharp, RNA interference—2001, *Genes Dev.*, 15: 485-90 (2001).
Soriaga et al., Determination of the orientation of aromatic molecules adsorbed on platinum electrodes. The effect of solute concentration. *J. Am. Chem. Soc.*, 104: 3937-45 (1982).
Stoeva et al., Multiplexed detection of protein cancer markers with biobarcoded nanoparticle probes, *J. Am. Chem. Soc.*, 128: 8378-9 (2006).
Storhoff et al., What controls the optical properties of DNA-linked gold nanoparticle assemblies? *J. Am. Chem. Soc.*, 122: 4640-50 (2000).
Thomas et al., The interaction of HgCl2 with sodium thymonucleate, *J. Am. Chem. Soc.*, 76:6032-4 (1954).
Thompkins et al., The study of the gas-solid interaction of acetic acid with a cuprous oxide surface using reflection-absorption spectroscopy, *J. Colloid Interface Sci.*, 49:410-21 (1974).
Timmons et al., Investigation of fatty acid monolayers on metals by contact potential measurements, *J. Phys. Chem.*, 69: 984-90 (1965).
Wang et al., Nanoparticles for multiplex diagnostics and imaging, *Nanomedicine (Lond.)*, 1: 413-26 (2006).
Wasserman et al., Structure and reactivity of alkylsiloxane monolayers formed by reaction of alkyltrichlorosilanes on silicon substrates, *Langmuir*, 5:1074-87 (1989).
Whitesides, *Proceedings of the Robert A. Welch Foundation 39th Conference on Chemical Research Nanophase Chemistry*, Houston, Texas, pp. 109-121 (1995).
Yamane et al., On the complexing of desoxyribonucleic acid (DNA) by mercuric ion, *J. Am. Chem. Soc.*, 83:2599-607 (1961).
Yang et al., Evidence that processed small dsRNAs may mediate sequence-specific mRNA degradation during RNAi in *Drosophila* embryos, *Curr. Biol.*, 10: 1191-200 (2000).
You et al., Engineering the nanoparticle-biomacromolecule interface, *Soft Matter*, 2:190-204 (2006).
Zamore et al., RNAi: double-stranded RNA directs the ATP-dependent cleavage of mRNA at 21 to 23 nucleotide intervals, *Cell*, 101: 25-33 (2000).
Zhang et al., An extremely stable and orthogonal DNA base pair with a simplifed three-carbon backbone, *J. Am. Chem. Soc.*, 127:74-5 (2005).
Zhang et al., PowerBlast: A new network BLAST application for interactive or automated sequence analysis and annotation, *Genome*, 7:649-56 (1997).
Zimmerman et al., A novel silver(I)-mediated DNA base pair, *J. Am. Chem. Soc.*, 124:13684-5 (2002).
International Search Report and Written Opinion from corresponding International application No. PCT/US2009/065822, mailing date Mar. 23, 2010.
International Preliminary Report on Patentability from corresponding International application No. PCT/US2009/065822, dated May 24, 2011.
Xu et al., Thermodynamics of DNA hybridization on gold nanoparticles, J. Am. Chem. Soc., 127:13227-31 (2005).
Third party observations filed in European Application No. 08756546.1 dated Apr. 25, 2012.
Third party observations filed in European Application No. 08756546.1 dated Oct. 29, 2012.
Agasti et al., Photoregulated release of caged anticancer drugs from gold nanoparticles, J. Am. Chem. Soc., 131(16):5728-9 (2009).
Agrawal et al., Antisence therapeutics: Is it as simple as complementary base recognition? *Mol. Med. Today*, 6: 72-81 (2000).
Ahmadi et al., Shape-controlled synthesis of colloidal platinum nanoparticles. Science, 272(5270): 1924-6 (1996).
Aime et al., Insights into the use of paramagnetic Gd(III) complexes in MR-molecular imaging investigations, J. Magn. Reson. Imaging, 16(4):394-406 (2002).
Aime et al., Pushing the sensitivity envelope of lanthanide-based magnetic resonance imaging (MRI) contrast agents for molecular imaging applications, Acc. Chem. Res., 42(7):822-31 (2009).
Alivisatos et al., Organization of 'nanocrystal molecules' using DNA. Nature, 382: 609-11 (1996).
Allara et al., The study of the gas-solid interaction of acetic acid with a cuprous oxide surface using reflection-absorption spectroscopy. J. Colloid Interface Sci., 49: 410-21 (1974).
Alric et al., Gadolinium chelate coated gold nanoparticles as contrast agents for both X-ray computed tomography and magnetic resonance imaging, J. Am. Chem. Soc., 130(18):5908-15 (2008).
Altieri, Survivin, versatile modulation of cell division and apoptosis in cancer, Oncogene, 22: 8581-9 (2003).
Amirkhanov et al., Design of (Gd-DO3A)n-polydiamidopropanoyl-peptide nucleic acid-D(Cys-Ser-Lys-Cys) magnetic resonance contrast agents. *Biopolymers*, 89(12): 1061-76 (2008).

(56) References Cited

OTHER PUBLICATIONS

Aynie, et al., Spongelike alginate nanoparticles as a new potential system for the delivery of antisense oligonucleotides. Antisense Nucl. Acid Drug Dev., 9: 301-12 (1999).
Bahnemann, Photochemical Conversion and Storage of Solar Energy, Pelizetti and Schiavello (Eds.) pp. 251-276 (1991).
Baker et al., Dendrimer-mediated cell transfection in vitro. Meth. Molec. Biol., 245: 67-81 (2004).
Bath et al., DNA nanomachines, Nat. Nanotechnol., 2: 275-84 (2007).
Baudhuim, Photochemical conversion and storage of solar energy. Kluwer Academic Publishers. 251-76 (1990).
Baudhuin et al., Molecular interactions between colloidal gold, proteins, and living cells. Chapter 1: 1-17 (1989).
Berton, et al., Highly loaded nanoparticulate carrier using an hydrophobic antisense oligonucleotide complex, Eur. J. Pharma. Sci., 9: 163-70 (1999).
Besch et al., Characterization and quantification of triple helix formation in chromosomal DNA. *J. Mol. Biol.*, 341: 979-89 (2004).
Bharali et al., Organically modified silica nanoparticles: a nonviral vector for in vivo gene delivery and expression in the brain. Proc. Natl. Acad. Sci. USA, 102(32): 11539-44 (2005).
Biancone et al., Magnetic resonance imaging of gadolinium-labeled pancreatic islets for experimental transplantation, NMR Biomed., 20(1):40-8 (2007).
Bielinska et al., DNA complexing with polyamidoamine dendrimers: implications for transfection. Bioconjug Chem., 10(5): 843-50 (1999).
Birck et al., Mutation and allelic loss of the PTEN/MMAC1 gene in primary and metastatic melanoma biopsies, J. Invest. Dermatol., 114: 277-80 (2000).
Bowman et al., Inhibition of HIV fusion with multivalent gold nanoparticles, J. Am. Chem. Soc., 130(22):6896-7 (2008).
Bramhill, Bacterial cell division, *Annu. Rev. Cell Dev. Biol.*, 13: 395-424 (1997).
Bratu et al., Visualizing the distribution and transport of mRNAs in living cells, Proc. Natl. Acad. Sci. USA, 100: 13308-13 (2003).
Brus, Quantum crystallites and nonlinear optics. Appl. Phys. A. 53(6): 465-74 (1991).
Capaccioli et al., Cationic lipids improve antisense oligonucleotide uptake and prevent degradation in cultured cells and inhuman serum, Biochem. Biophys. Res. Commun., 197(2): 818-25 (1993).
Caravan et al., The interaction of MS-325 with human serum albumin and its effect on proton relaxation rates, J. Am. Chem. Soc., 124(12):3152-62 (2002).
Caravan, Strategies for increasing the sensitivity of gadolinium based MRI contrast agents, Chem. Soc. Rev., 35(6):512-23 (2006).
Castoldi et al., A sensitive array for microRNA expression profiling (miChip) based on locked nucleic acids (LNA), RNA. 12: 913-20 (2006).
Charreyre et al., Fluorescence energy transfer study of the conformation of oligonucleotides covalently bound to polystyrene latex particles. Langmuir, 13: 3103-10 (1997).
Chavany et al., Polyalkylcyanoacrylate nanoparticles as polymeric carriers for antisense oligonucleotides, Pharma. Res., 9(4): 441-9 (1992).
Chavany, et al., Adsorption of oligonucleotides onto polyisohexylcyanoacrylate nanoparticles protects them against nucleases and increases their cellular uptake. Pharma. Res., 11(9): 1370-8 (1994).
Chen et al., Kinetics and thermodynamics of DNA hybridization on gold nanoparticles, Nucl. Acids Res., 37: 3756-65 (2009).
Cheung et al., Akt3 and mutant V600E B-Raf cooperate to promote early melanoma development, Cancer Res., 68:3429-39 (2008).
Chirila et al., The use of synthetic polymers for delivery of therapeutic antisense oligodeoxynucleotides. *Biomaterials*, 23: 321-42 (2002).
Chithrani et al., Elucidating the mechanism of cellular uptake and removal of protein-coated gold nanoparticles of different sizes and shapes. Nano Lett., 7: 1542-50 (2007).

Chithrani, et al., Determining the size and shape dependence of gold nanoparticle uptake into mammalian cells, Nano Lett., 6(4): 662-8 (2006).
Chrisey et al., Covalent attachment of synthetic DNA to self-assembled monolayer films, Nucl. Acids Res., 24: 3031-9 (1996).
Cload et al., Polyether tethered oligonucleotide probes. J. Am. Chem. Soc., 113(16): 6324-6 (1991).
Crawford et al., A novel B-RAF inhibitor blocks interleukin-8 (IL-8) synthesis in human melanoma xenografts, revealing IL-8 as a potential pharmacodynamic biomarker, Mol. Cancer Ther., 7: 492-9 (2008).
Crawford et al., Peptide aptamers: Tools for biology and drug discovery. 2(1): 72-9 (2003).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. *Ann. Rev. Med.*, 55: 61-95 (2004).
Curtis et al., A morphology-selective copper organosol. Angew. Chem. Int. Ed. Engl., 27: 1530-3 (1988).
Daniel et al., Gold nanoparticles: assembly, supramolecular chemistry, quantum-size-related properties, and applications toward biology, catalysis, and nanotechnology. Chem Rev., 104(1): 293-346 (2004).
Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
Debouttiere et al., Design of gold nanoparticles for magnetic resonance imaging. Adv. Funct. Mater., 16:2330 (2006).
DeMesmaeker et al., Antisense oligonucleotides. Acc. Chem. Res., 28(9): 366-74 (1995).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. *J. Am. Chem. Soc.*, 131(41): 14652-3 (2009).
Dhar et al., Targeted single wall carbon nanotube mediated Pt(IV) prodrug delivery using folate as a homing device. *J. Am. Chem. Soc.*, 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli*., *Annu. Rev. Microbiol.*, 47: 199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., Circular dichroism studies of an oligodeoxyribonucleotide containing a hairpin loop made of a hexaethylene glycol chain: conformation and stability. Nucl. Acids Res. , 18(21): 6353-9 (1990).
Dykxhoorn et al., Killing the messenger: short RNAs that silence gene expression, Nat. Rev. Mol. Cell Biol., 4(6):457-67 (2003).
Eckstein (Ed.), Oligonucleotides and analogues, 1st Ed., Oxford University Press, New York (1991).
Elaissari et al., Effect of charge nature on the adsorption of single-stranded DNA fragments onto latex particles. J. Colloid Interface Sci., 202: 251-60 (1998).
Endres et al., DNA-Ti02 nanoconjugates labeled with magnetic resonance contract agents. *J. Am. Chem. Soc.* 129(51): 15760-1 (2007).
Fahy et al., Design and synthesis of polyacrylamide-based oligonucleotide supports for use in nucleic acid diagnostics, Nucl. Acids Res., 21: 1819-26 (1993).

(56) References Cited

OTHER PUBLICATIONS

Fattal et al., Biodegradable polyalkylcyanoacrylate nanoparticles for the delivery of oligonucleotides. J. Control Rel., 53(1-3): 137-43 (1998).
Femino et al., Visualization of single RNA transcripts in situ. Science, 280: 585-90 (1998).
Ferentz et al., Disulfide-crosslinked oligonucleotides. J. Am. Chem. Soc., 113(10): 4000-2 (1991).
Flandroy et al., (D, L)Polyactide microspheres as embolic agent. *Neuroradiology*, 32: 311-5 (1990).
Frullano et al., Multimodal MRI contrast agents, J. Biol. Inorg. Chem., 12(7):939-40 (2007).
Gao et al., Secondary structure effects on DNA hybridization kinetics: a solution versus surface comparison. Nucl. Acids Res., 34: 3370-7 (2006).
Gerdes et al., Experimental determination and system level analysis of essential genes in *Escherichia coli* MG1655. *J. Bacteriol.*, 185: 5673-84 (2003).
Gidwani et al., Hybridization kinetics of double-stranded DNA probes for rapid molecular analysis. Analyst, 134: 1675-81 (2009).
Giljohann et al., Gene regulation with polyvalent siRNA-nanoparticle conjugates. J. Am. Chem. Soc., 131:2072-3 (2009).
Goel et al., Melanocytic nevus-like hyperplasia and melanoma in transgenic BRAFV600E mice. Oncogene, 28: 2289-98 (2009).
Guo et al., CELL-SELEX: Novel perspectives of aptamer-based therapeutics, Int. J. Mol. Sci., 9: 668-78 (2008).
Hale et al., Recruitment of ZipA to the septal ring of *Escherichia coli* is dependent on FtsZ and independent of FtsA. *J. Bacteriol.*, 181: 167-76 (1999).
Han et al., A gold nanoparticle based approach for screening triplex DNA binders, J. Am. Chem. Soc., 128(15):4954-5 (2006).
Hayat, (Ed.) Colloidal Gold: Principles, Methods, and Applications, vol. 1, Table of Contents, pp. v-xvii; vol. 2, Table of Contents pp. v-xix; vol. 3, Table of Contents, ppv-xiv, Academic Press, San Diego (1989-1991).
He et al., Colloidal Au-enhanced surface plasmon resonance for ultrasensitive detection of DNA hybridization. J. Am. Chem. Soc., 122(38): 9071-7 (2000).
Henglein et al., Absorption spectrum and some chemical reactions of colloidal platinum in aqueous solution. J. Phys. Chem., 99(38): 14129-36 (1995).
Henglein, Mechanism of reactions on colloidal microelectrodes and size quantization effects. Top. Curr. Chem., 143: 113-80 (1998).
Henglein, Small-particle research: physicochemical properties of extremely small colloidal metal and semiconductor particles. Chem. Rev., 89(8): 1861-73 (1989).
Holen et al., Positional effects of short interfering RNAs targeting the human coagulation trigger tissue factor. *Nucl. Acids Res.*, 30: 1757-66 (2002).
Hu et al., Advances in high-field magnetic resonance imaging, Annu. Rev. Biomed.Eng., 6:157-84 (2004).
Hussain et al., A novel anionic dendrimer for improved cellular delivery of antisense oligonucleotides. J. Controlled Rel., 99: 139-55 (2004).
Introducing Antisense Oligonucleotides into Cells, Innovation & Precision in Nucleic Acid Synthesis, Integrated DNA Technologies (2005).
Jackson et al., *Escherichia coli* O157:H7 diarrhoea associated with well water and infected cattle on an Ontario farm, *Epidemiol. Infect.*, 120:17-20 (1998).
Jackson et al., How do microRNAs regulate gene expression?, Sci STKE, 2007(367):re1 (2007).
Jaschke et al., Automated incorporation of polyethylene glycol in synthetic oligonucleotides. Tetrahedron Lett., 34: 301-4 (1993).
Jason et al., Toxicology of antisense therapeutics. Toxicol. Appl. Pharmacol., 201(1): 66-83 (2004).
Jen et al., A nonviral transfection approach in vitro: the design of a gold nanoparticle vector joint with microelectromechanical systems. Langmuir, 20(4): 1369-74 (2004).
Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).
Kalman et al., Potentiometric and relaxometric properties of a gadolinium-based MRI contrast agent for sensing tissue pH, Inorg. Chem., 46(13):5260-70 (2007).
Katz et al., Integrated nanoparticle-biomolecule hybrid systems: synthesis, properties, and applications, Angew. Chem. Int. Ed., 43: 6042-108 (2004).
Kim et al., Biodegradable quantum dot nanocomposites enable live cell labeling and imaging of cytoplasmic targets, Nano Lett., 8(11):3887-92 (2008).
Kloosterman et al., In situ detection of miRNAs in animal embryos using LNA-modified oligonucleotide probes, Nat. Methods, 3: 27-9 (2006).
Kolarova et al., Preparation of magnetic oligo (dT) particles, Biotechniques, 20: 196-8 (1996).
Kopylov et al., Combinatorial chemistry of nucleic acids: SELEX, Mol. Biol., 34: 940-54 (2000).
Kroschwitz (Ed.), The Concise Encyclopedia of Polymer Science and Engineering, pp. 858-859, John Wiley & Sons (1990).
Kukowska-Latallo et al., Efficient transfer of genetic material into mammalian cells using Starburst polyamidoamine dendrimers, Proc. Natl. Acad. Sci. USA, 93: 4897-902 (1996).
Lannutti et al., Human angiostatin inhibits murine hemangioendothelioma tumor growth in vivo, Cancer Res., 57: 5277-80 (1997).
Lebedeva et al., Antisense oligonucleotides: Promise and reality. Annu. Rev. Pharmacol. Toxicol., 41: 403-19 (2001).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, *Biochem. J.*, 303: 1-14 (1994).
Leslie et al., A new tool for oligonucleotides import into cells. Clin. Chem., 55: 609-10 (2009).
Leunissen et al., Switchable self-protected attractions in DNA-functionalized colloids. Nat. Mater., 8: 590-95 (2009).
Li et al., A calcium-sensitive magnetic resonance imaging contrast agent. J. Am. Chem. Soc., 121 :1413 (1999).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Lipshutz et al., High density synthetic oligonucleotide arrays. Nanotechnology, 14: R15-27 (2003).
Liu et al., ARDB—Antibiotic Resistance Genes Database. *Nucl. Acids Res.*, 37: D443-7 (2009).
Liu et al., Argonaute2 is the catalytic engine of mammalian RNAi. Science, 305(5689): 1437-41 (2004).
Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., New poly(d-glucaramidoamine)s induce DNA nanoparticle formation and efficient gene delivery into mammalian cells. J. Am. Chem. Soc., 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Liu et al., Synthesis, stability, and cellular internalization of gold nanoparticles containing mixed peptide-poly(ethylene glycol) monolayers. Anal. Chem., 79: 2221-9 (2007).
Loeken, Effects of mutation of the CREB binding site of the somatostatin promoter on cyclic AMP responsiveness in CV-1 cells. *Gene Expr.*, 3: 253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring. *Annu. Rev. Biochem.*, 66: 93-116 (1997).

(56) References Cited

OTHER PUBLICATIONS

Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).
Ma et al., Design and synthesis of RNA miniduplexes via a synthetic linker approach. Biochemistry, 32(7): 1751-8 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, Preparation of aqueous magnetic liquids in alkaline and acidic media. IEEE Transactions on Magnetics. 17(2): 1247-8 (1981).
Matsuura et al., Construction and characterization of protein libraries composed of secondary structure modules. Protein Sci., 11: 2631-43 (2002).
Mattson et al., A practical approach to crosslinking. *Molec. Biol. Rep.*, 17: 167-83 (1993).
Maxwell et al., Self-assembled nanoparticle probes for recognition and detection of biomolecules. J. Am. Chem. Soc., 124: 9606-12 (2002).
Maye et al., A simple method for kinetic control of DNA-induced nanoparticle assembly. J. Am. Chem. Soc., 128: 14020-1 (2006).
Mayer (ed.), Nucleic Acid and Peptide Aptamers: Methods and Protocols (Humana Press, 2009).
McCurdy et al., Deoxyligonucleotides with inverted polarity: Synthesis and use in triple-helix formation. Nucleosides & Nucleotides, 10: 287-90 (1991).
McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).
McKenzie et al., Sequence-specific DNA detection using high-affinity LNA-functionalized gold nanoparticles. Small, 3(11): 1866-8 (2007).
McManus et al., Gene silencing in mammals by small interfering RNAs. Nat. Rev. Genet, 3(10): 737-47 (2002).
Mendell, MicroRNAs: critical regulators of development, cellular physiology and malignancy, Cell Cycle, 4(9):1179-84 (2005).
Miller et al., Antisense oligonucleotides: Strategies for delivery. PSTT, 1(9): 377-86 (1998).
Milne et al., An approach to gene-specific transcription inhibition using oligonucleotides complementary to the template strand of the open complex. *Proc. Natl. Acad. Sci. USA*, 97(7): 3136-41 (2000).
Mittal, Improving the efficiency of RNA interference in mammals, Nat. Rev. Genet., 5(5):355- 65 (2004).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Myers et al., A cyclopentane conformational restraint for a peptide nucleic acid: design, asymmetric synthesis, and improved binding affinity to DNA and RNA. Org Lett., 5(15): 2695-8 (2003).
Nitin et al., Peptide-linked molecular beacons for efficient delivery and rapid mRNA detection in living cells. Nucl. Acids Res., 32: e58 (2004).
Ohuchi et al., In vitro method for the generation of protein libraries using PCR amplification of a single DNA molecule and coupled transcription/translation, Nucl. Acids Res., 26: 4339-46 (1998).

Olshaysky et al., Organometallic synthesis of gallium-arsenide crystallites, exhibiting quantum confinement. J. Am. Chem. Soc., 112(25): 9438-9 (1990).
O'Meara et al., Capture of single-stranded DNA assisted by oligonucleotide modules. Anal. Biochem., 255: 195-203 (1998).
Ono et al., DNA triplex formation of oligonucleotide analogues consisting of linker groups and octamer segments that have opposite sugar-phosphate backbone polarities. Biochemistry, 30(41): 9914-2 (1991).
Opalinska et al., Nucleic-acid therapeutics: basic principles and recent applications. Nat. Rev. Drug Discov., 1: 503-14 (2002).
O'Reilly et al., Identification of an activating transcription factor (ATF) binding site in the human transforming growth factor-beta 2 promoter. *J. Biol. Chem.*, 267: 19938-43 (1992).
Ow Sullivan et al., Development of a novel gene delivery scaffold utilizing colloidal gold-polyethylenimine conjugates for DNA condensation. Gene Ther., 10(22): 1882-90 (2003).
Parak et al., Biological applications of colloidal nanocrystals, Nanotechnol., 14: R15-27 (2003).
Park et al., Array-based electrical detection of DNA with nanoparticle probes. Science, 295: 1503-6 (2002).
Park et al., Gold nanoparticles functionalised by Gd-complex of DTPA-bis(amide) conjugate of glutathione as an MRI contrast agent, Bioorg. Med. Chem. Lett., 18(23):6135-7 (2008).
Patel et al., Peptide antisense nanoparticles. Proc. Natl. Acad. Sci. USA, 105: 17222-6 (2008).
Patil et al., DNA-based therapeutics and DNA delivery systems: a comprehensive review. AAPS J., 7(1): E61-77 (2005).
Paunecku et al., Godolinium-conjugated Ti02-DNA oligonucleotide nanoconjugates show prolonged intracellular retention period and T1-weighted contract enhancement in magnetic resonance images. *Nanomedicine*, 4(3): 201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. *Rev. Med. Virol.*, 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis. *Meth. Molec. Biol.*, 20: 465-96 (1993).
Prausnitz et al., Transdermal drug delivery, Nat. Biotechnol., 26: 1261-8 (2008).
Prigodich et al., Nano-flares for mRNA regulation and detection. ACS Nano, 3: 2147-52 (2009).
Prime et al., Self-assembled organic monolayers; Model systems for studing adsorption of proteins at surfaces. Science, 252: 1164-7 (1991).
Raj et al., Stochastic mRNA synthesis in mammalian cells. PLoS Biol., 4(10): e309 (2006).
Rethore et al., Preparation of chitosan/polyglutamic acid spheres based on the use of polystyrene template as nonviral gene carrier. *Tissue Engineering*, 15(4): 605-13 (2009).
Riccelli et al., Hybridization of single-stranded DNA targets to immobilized complementary DNA probes: comparison of hairpin versus linear capture probes. Nucl. Acids Res., 29: 996-1004 (2001).
Richardson et al., Tethered oligonucleotide probes. A strategy for the recognition of structured RNA. J. Am. Chem. Soc., 113(13): 5109-11 (1991).
Rihova et al., Receptor-mediated targeted drug or toxin delivery. Adv. Drug Deliv. Rev., 29(3): 273-89 (1998).
Rizzo et al., Chimeric RNA-DNA molecular beacon assay for ribonuclease H activity. Mol. Cell Probes, 16: 277-83 (2002).
Rosi et al., Nanostructures in biodiagnostics. Chem Rev., 105(4): 1547-62 (2005).
Rosi et al., Oligonucleotide-modified gold nanoparticles for intracellular gene regulation. Science, 2312(5776): 1027-30 (2006).
Sambrook et al., Molecular Cloning: A Laboratory Manual, 2nd Edition, Table of Contents, pp. v-xxxii (1989).
Sandhu et al., Gold nanoparticle-mediated transfection of mammalian cells. Bioconjugate Chem., 13: 3-6 (2002).

(56) References Cited

OTHER PUBLICATIONS

Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Schifferlers et al., Cancer siRNA therapy by tumor selective delivery with ligand-targeted sterically stabilized nanoparticle. *Nucl. Acid Res.*, 32(19): e149 (2004).
Schmid, G. (ed.) Clusters and Colloids (VCH, Weinheim, 1994).
Seela et al., Oligodeoxyribonucleotides containing 1,3-propanediol as nucleoside substitute. Nucl. Acids Res., 15(7): 3113-29 (1987).
Seelig et al., Catalyzed relaxation of a metastable DNA fuel. J. Am. Chem. Soc., 128: 12211- 20 (2006).
Seferos et al., Locked nucleic acid-nanoparticle conjugates. Chembiochem., 8: 1230-2 (2007).
Seferos et al., Nano-flares: probes for transfection and mRNA detection in living cells. J. Am. Chem. Soc., 129: 15477-9 (2007).
Seferos et al., Polyvalent DNA nanoparticle conjugates stabilize nucleic acids. Nano Lett., 9: 308-11 (2009).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15:.1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Simmel et al., DNA nanodevices. Small, 1: 284-99 (2005).
Smith et al., Bioconjugated quantum dots for in vivo molecular and cellular imaging, Adv. Drug Deliv. Rev., 60(1 1):1226-40 (2008).
Sokol et al., Real time detection of DNA.RNA hybridization in living cells. Proc. Natl. Acad. Sci. USA, 95: 11538-43 (1998).
Song et al., Synthesis of multimeric MR contrast agents for cellular imaging, J. Am. Chem. Soc., 130(21):6662-3 (2008).
Srivastava et al., Use of riboprobes for northern blotting analysis. Biotechniques, 11(5): Abstract (1991).
Stahl et al., Deregulated Akt3 activity promotes development of malignant melanoma, Cancer Res., 64: 7002-10 (2004).
Stephenson et al., Inhibition of Rous sarcoma viral RNA translation by a specific oligodeoxyribonucleotide. Proc. Natl. Acad. Sci. USA, 75(1): 285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).
Taton et al., Scanometric DNA array detection with nanoparticle probes, Science, 289(5485):1757-60 (2000).
Thomas et al., Conjugation to gold nanoparticles enhances polyethylenimine's transfer of plasmid DNA into Mammalian cells. Proc. Natl. Acad. Sci. USA, 100(16):9138-43 (2003).
Thurn et al., Labeling Ti02 nanoparticles with dyes for optical fluorescence microscopy and determination of Ti02-DNA nanoconjugate stability. *Small*, 5(11): 1318-25 (2009).
Tkachenko et al., Cellular trajectories of peptide-modified gold particle complexes: comparison of nuclear localization signals and peptide transduction domains. Bioconjugate Chem., 15(3): 482-90 (2004).
Tkachenko et al., Multifunctional gold nanoparticle-peptide complexes for nuclear targeting. J. Am. Chem. Soc., 125: 4700-1 (2003).
Tondelli, et al., Highly efficient cellular uptake of c-myb antisense oligonucleotides through specifically designed polymeric nanospheres. Nucl. Acids Res., 26: 5425-31 (1998).

Treisman, The SRE: a growth factor responsive transcriptional regulator. *Semin. Cancer Biol.*, 1: 47-58 (1990).
Tsao et al., Genetic interaction between NRAS and BRAF mutations and PTEN/MMAC1 inactivation in melanoma. J. Invest. Dermatol., 122: 337-41 (2004).
Tuerk et al., Systematic evolution of ligands by exponential enrichment: RNA ligands to bacteriophage T4 DNA polymerase. Science, 249: 505-10 (1990).
Turberfield et al., DNA fuel for free-running nanomachines. Phys. Rev. Lett., 90: 118102 (2003).
Tyagi et al., Molecular beacons: Probes that fluoresce upon hybridization. Nat. Biotechnol., 14: 303-8 (1996).
Uchida et al., GaAs nanocrystals prepared in quinoline. *J. Phys. Chem.* 95(14): 5382-4 (1991).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wagner et al., Gene inhibition using antisense oligodeoxynucleotides. Nature, 372: 333-5 (1994).
Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).
Wang et al., Inhibition of integrin-linked kinase/protein kinase B/Akt signaling: mechanism for ganglioside-induced apoptosis. J. Biol. Chem., 276: 44504-11 (2001).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanometer-sized semiconductor clusters: materials synthesis, quantum size effects, and photophysical properties. J. Phys. Chem., 95(2): 525-32 (1991).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@C nanoparticles: isolation, structure, magnetic properties, and directed assembly, Nano Lett., 8(11):3761-5 (2008).
Watson et al. (Eds.), *Molecular Biology of the Gene*, 4th ed., the Benjamin/Cummings Publishing Company Inc. (1987).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Weller, Colloidal Semiconductor Q-particles: Chemistry in the transition region between solid state and molecules. Angew. Chem. Int. Ed. Engl., 32(1): 41-53 (1993).
Winter et al., Molecular imaging by MRI, Curr. Cardiol. Rep. 8(1):65-9 (2006).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Xu et al., Thermodynamics of DNA hybridization on gold nanoparticles. J. Am. Chem. Soc., 127(38): 13227-31 (2005).
Yan et al., Aptamers and aptamer targeted delivery. RNA Biol., 6: 316-20 (2009).

(56) References Cited

OTHER PUBLICATIONS

Ye et al., Characterization of a silencer regulatory element in the human interferon-gamma promoter. J. Biol. Chem., 269: 25728-34 (1994).
Yin Win et al., Effects of particle size and surface coating on cellular uptake of polymeric nonparticles for oral delivery of anticancer drugs. Biomaterials, 26: 2713-22 (2005).
You et al., Detection and identification of proteins using nanoparticle-fluorescent polymer 'chemical nose' sensors. Nat. Nanotechnol., 2: 318-23 (2007).
Zabner et al., Cellular and molecular barriers to gene transfer by a cationic lipid. J. Biol. Chem., 270: 18997-9007 (1995).
Zamecnik et al., Inhibition of Rous sarcoma virus replication and cell transformation by a specific oligodeoxynucleotide. Proc. Natl. Acad. Sci. USA, 75(1): 280-4 (1978).
Zhang et al., Control of DNA strand displacement kinetics using toehold exchange. J. Am. Chem. Soc., 131: 17303-14 (2009).
Zhang et al., Single-quantum-dot-based DNA sensor. Nat. Mater., 4: 826-31 (2005).
Zheng et al., Aptamer nano-flares for molecular detection in living cells. Nano Lett., 9: 3258-61 (2009).
Zimmer, Antisense oligonucleotide delivery with polyhexylcyanoacrylate nanoparticles as carriers. Methods, 18: 286-95 (1999).
Alivisatos, The use of nanocrystals in biological detection, Nat. Biotechnol., 22(1):47-52 (2004).
Angelini et al., Reversal of P-glycoprotein-mediated multidrug resistance in human sarcoma MES-SA/Dx-5 cells by nonsteroidal anti-inflammatory drugs, Oncol. Rep., 20(4):731-5 (2008).
Anton et al., Design and production of nanoparticles formulated from nano-emulsion templates-a review, J. Control Release, 128(3):185-99 (2008).
Balasubramanian et al., Biodistribution of gold nanoparticles and gene expression changes in the liver and spleen after intravenous administration in rats, Biomaterials, 31 (8):2034-42 (2010).
Bardeesy et al., Pancreatic cancer biology and genetics, Nat. Rev. Cancer, 2(12):897-909 (2002).
Bisht et al., Polymeric nanoparticle-encapsulated curcumin ("nanocurcumin"): a novel strategy for human cancer therapy, J. Nanobiotechnology, 5:3 (2007) (18 pages).
Brown et al., Surface treatment of the hydrophobic drug danazol to improve drug dissolution, Int. J. Pharmaceutics, 165:227-37 (1998).
Cao et al., Raman dye-labeled nanoparticle probes for proteins, J. Am. Chem. Soc., 125(48):14676-7 (2003).
Cha et al., Hepatocellular carcinoma: current management, Curr. Probl. Surg., 47(1):10-67 (2010).
Chari et al., Immunoconjugates containing novel maytansinoids: promising anticancer drugs, Cancer Res., 52(1):127-31 (1992).
Chen et al., MDR 1 activation is the predominant resistance mechanism selected by vinblastine in MES-SA cells, Br. J. Cancer, 83(7):892-8 (2000).
Cheng et al., Tandem synthesis of core-shell brush copolymers and their transformation to peripherally cross-linked and hollowed nanostructures, J. Am. Chem. Soc., 128(21):6808-9 (2006).
Chompoosor et al., Charge dependence of ligand release and monolayer stability of gold nanoparticles by biogenic thiols, Bioconjugate Chem., 19:1342-5 (2008).
Chu et al., Effects of photoactivated 5-aminolevulinic acid hexyl ester on MDR1 over-expressing human uterine sarcoma cells, Toxicol. Lett., 181(1):7-12 (2008).
Connor et al., Gold nanoparticles are taken up by human cells but do not cause acute cytotoxicity, Small, 1(3):325-7 (2005).
Deutsch et al., Synthesis of congeners and prodrugs. 3. Water-soluble prodrugs of taxol with potent antitumor activity, J. Med. Chem., 32(4):788-92 (1989).
Examination Report from European Application No. 08729548.1, dated Jan. 19, 2010.
Final Office Action issued in connection with U.S. Appl. No. 11/917,680, dated Nov. 10, 2010.
Final Office Action issued in connection with U.S. Appl. No. 11/917,680, dated Nov. 10, 2011.
Final Office Action issued in connection with U.S. Appl. No. 12/130,643, dated Jun. 16, 2011.
Frens, Particle size and sol stability in metal colloids, Kolloid-Zeitschrift and Zeitschrift fur Polymere, 250(7):736-41 (1972).
Fukuda et al., Effective transformation of unactivated alkynes into ketones or acetals by means of Au(III) catalyst, J. Org. Chem., 56(11):3729-31 (1991).
Fukuda et al., Efficient transformation of methyl propargyl ethers into alpha,beta-unsaturated ketones, Bull. Chem. Soc. Jpn., 64:2013-5 (1991).
Furstner et al., Catalytic carbophilic activation: catalysis by platinum and gold pi acids, Angew Chem Int Ed Engl., 46(19):3410-49 (2007).
Gavrieli et al., Identification of programmed cell death in situ via specific labeling of nuclear DNA fragmentation, J. Cell Biol., 119(3):493-501 (1992).
Ghosh et al., Gold nanoparticles in delivery applications, Adv. Drug Deliv. Rev. 60(11):1307-15 (2008).
Gibson et al., Paclitaxel-functionalized gold nanoparticles, J. Am. Chem. Soc., 129(37):11653-61 (2007).
Giljohann et al., Gold nanoparticles for biology and medicine, Angew Chem. Int. Ed. Engl., 49(19):3280-94 (2010).
Goodrich et al., Non-coding-RNA regulators of RNA polymerase II transcription, Nat. Rev. Mol. Cell Biol., 7(8):612-6 (2006).
Grabar et al., Preparation and characterization of Au colloid monolayers, Anal. Chem., 67:735- 43 (1995).
Hames et al. (eds.), Gene Probes 1, New York: IRL Press (1995).
Hashmi et al., Gold catalysis, Angew Chem Int Ed Engl., 45(47):7896-936 (2006).
Hashmi et al., Gold-catalyzed organic reactions, Chem. Rev., 107:3180-211 (2007).
Hegner et al., Modified DNA immobilized on bioreactive self-assembled monolayer on gold for dynamic force microscopy imaging in aqueous buffer solution, J. Vac. Sci. Technol. B, 14(2):1418-21 (1996).
Hu et al., Hollow chitosan/poly(acrylic acid) nanospheres as drug carriers, Biomacromolecules, 8(4):1069-76 (2007).
Hurst et al., "Multisegmented one-dimensional nanorods prepared by hard-template synthetic methods," Angew. Chem. Int. Ed. Engl., 45:2672-2692 (2006).
Hwu et al., Targeted Paclitaxel by conjugation to iron oxide and gold nanoparticles, J. Am. Chem. Soc., 131 (1):66-8 (2009).
International Preliminary Report on Patentability for corresponding international applicaton No. PCT/US2010/047594, dated Mar. 6, 2012.
International Preliminary Report on Patentability for International Application No. PCT/US10/62047, issuance date Jun. 26, 2012.
International Preliminary Report on Patentability for International Application No. PCT/US2006/022325, dated Dec. 17, 2007.
International Preliminary Report on Patentability for International Application No. PCT/US2008/053603, dated Aug. 11, 2009.
International Preliminary Report on Patentability for International Application No. PCT/US2008/065366, dated Dec. 1, 2009.
International Preliminary Report on Patentability for International Application No. PCT/US2010/020558, dated Jul. 12, 2011.
International Preliminary Report on Patentability for International Application No. PCT/US2010/044453, dated Feb. 7, 2012.
International Preliminary Report on Patentability for International Application No. PCT/US2010/044844, dated Feb. 7, 2012.
International Preliminary Report on Patentability for Itnernational Application No. PCT/US2010/55018, dated May 1, 2012.
International Preliminary Report on Patentability, PCT/US2010/27363, dated Oct. 18, 2011.
International Preliminary Report on Patentability, PCT/US2010/47591, dated Mar. 6, 2012.
International Preliminary Report on Patentability, PCT/US2010/47594, dated Mar. 6, 2012.
International Search Report and Written Opinion for corresponding international application No. PCT/US10/47594, mailing date Oct. 20, 2010.
International Search Report and Written Opinion for International Application No. PCT/US10/62047, mailing date May 6, 2011.

(56) References Cited

OTHER PUBLICATIONS

International Search Report and Written Opinion for International Application No. PCT/US2006/022325, dated Oct. 20, 2006.
International Search Report and Written Opinion for International Application No. PCT/US2008/053603, dated Jul. 30, 2008.
International Search Report and Written Opinion for International Application No. PCT/US2008/065366, dated Aug. 28, 2008.
International Search Report and Written Opinion for International Application No. PCT/US2010/020558, dated Mar. 9, 2010.
International Search Report and Written Opinion for International Application No. PCT/US2010/044453, dated Apr. 29, 2011.
International Search Report and Written Opinion for International Application No. PCT/US2010/044844, dated Apr. 27, 2011.
International Search Report and Written Opinion for International Application No. PCT/US2010/27363, dated Apr. 15, 2010.
International Search Report and Written Opinion for International Application No. PCT/US2010/47591, dated Oct. 4, 2010.
International Search Report and Written Opinion for International Application No. PCT/US2010/47594, dated Oct. 8, 2010.
International Search Report and Written Opinion for International Application No. PCT/US2010/55018, dated Dec. 9, 2010.
Jin et al., Radiosensitization of paclitaxel, etanidazole and paclitaxel+etanidazole nanoparticles on hypoxic human tumor cells in vitro, Biomaterials, 28(25):3724-30 (2007).
Kan et al., Distribution and effect of iodized poppyseed oil in the liver after hepatic artery embolization: experimental study in several animal species, Radiology, 186(3):861-6 (1993).
Kan et al., Role of Kupffer cells in iodized oil embolization, Invest. Radiol., 29(11):990-3 (1994).
Kasuya et al., Chapter 8—Bio-nanocapsule-liposome conjugates for in vivo pinpoint drug and gene delivery, Methods Enzymol., 464:147-66 (2009).
Kim et al., Direct synthesis of polymer nanocapsules with a noncovalently tailorable surface, Angew. Chem. Int. Ed. Engl., 46(19):3471-4 (2007).
Kim et al., Direct synthesis of polymer nanocapsules: self-assembly of polymer hollow spheres through irreversible covalent bond formation, J. Am. Chem. Soc., 132(28):9908-19 (2010).
Kim et al., Facile, template-free synthesis of stimuli-responsive polymer nanocapsules for targeted drug delivery, Angew. Chem. Int. Ed. Engl., 49(26):4405-8 (2010).
Kondo et al., Nanotube formation through the continuous one-dimensional fusion of hollow nanocapsules composed of layer-by-layer poly(lactic acid) stereocomplex films, J. Am. Chem. Soc., 132(24):8236-7 (2010).
Kosturko et al., The crystal and molecular structure of a 2:1 complex of 1-methylthyminemercury(II), Biochemistry, 13:3949-52 (1974).
Krutzfeldt et al., Silencing of microRNAs in vivo with 'antagomirs', Nature, 438(7068):685-9 (2005).
Landfester et al., From polymeric particles to multifunctional nanocapsules for biomedical applications using the miniemulsion process, J. Polymer Sci. Part A, 48(3):493-515 (2010).
Lee et al., Chip-based scanometric detection of mercuric ion using DNA-functionalized gold nanoparticles, Anal. Chem., 80(17):6805-8 (2008).
Lewis, "Controlled release of bioactive agents from lactide/glycolide polymer", pp. 1-41, IN: Chasin et al. (eds.), Biodegradable Polymers as Drug Delivery Systems, Marcel Dekker (1990).
Li et al., Dual-reactive surfactant used for synthesis of functional nanocapsules in miniemulsion, J. Am. Chem. Soc., 132(23):7823-5 (2010).
Li et al., Gold-catalyzed organic transformations, Chem. Rev., 108(8):3239-65 (2008).
Li et al., Reversible and chemically programmable micelle assembly with DNA block-copolymer amiphiphiles, Nano Lett., 4(6):1055-8 (2004).
Link et al., Size and temperature dependence of the plasmon absorption of colloidal gold nanoparticles, J. Phys. Chem. B, 103(21):4212-7 (1999).
Liu et al., Cross-linked polynorbornene-coated gold nanoparticles: dependence of particle stability on cross-linking position and cross-linker structure, Langmuir, 24:11169-74 (2008).
Liu et al., DNA-based micelles: synthesis, micellar properties and size-dependent cell permeability, Chemistry, 16(12):3791-7 (2010).
Llovet et al., Arterial embolisation or chemoembolisation versus symptomatic treatment in patients with unresectable hepatocellular carcinoma: a randomised controlled trial, Lancet, 359(9319):1734-9 (2002).
Merbach et al. (eds.), The Chemistry of Contrast Agents in Medical Magnetic Resonance Imaging, 1st ed., New York: Wiley (2001).
Modo et al. (eds.), Molecular and Cellular MR Imaging, Florida: CRC Press (2007).
Moughton et al., Hollow nanostructures from self-assembled supramolecular metallo-triblock copolymers, Soft Matter, 5(12):2361-70 (2009).
Non-Final Office Action issued in connection with U.S. Appl. No. 11/917,680, dated Jun. 8, 2011.
Non-Final Office Action issued in connection with U.S. Appl. No. 12/130,643, dated Jan. 13, 2011.
Non-Final Office Action issued in connection with U.S. Appl. No. 12/526,560, dated Mar. 15, 2012.
Non-Final Office Action issued in connection with U.S. Appl. No. 12/684,836, dated Jan. 6, 2012.
Non-Final Office Action issued in connection with U.S. Appl. No. 12/684,836, dated May 17, 2012.
Non-Final Office Action issued in connection with U.S. Appl. No. 12/724,395, dated Feb. 17, 2012.
Notice of Allowance issued in connection with U.S. Appl. No. 11/917,680, dated Apr. 26, 2012.
Ohishi et al., Hepatocellular carcinoma detected by iodized oil. Use of anticancer agents, Radiology, 154(1):25-9 (1985).
Okayasu et al., Selective and persistent deposition and gradual drainage of iodized oil, Lipiodol in the hepatocellular carcinoma after injection into the feeding hepatic artery, Am. J. Clin. Pathol., 90(5):536-44 (1988).
Ozpolat et al., Nanomedicine based approaches for the delivery of siRNA in cancer, J. Intern. Med., 267(1):44-53 (2010).
Paciotti et al., Colloidal gold: a novel nanoparticle vector for tumor directed drug delivery, Drug Deliv., 11(3):169-83 (2004).
Patel et al., Scavenger receptors mediate cellular uptake of polyvalent oligonucleotide-functionalized gold nanoparticles, Bioconjug. Chem., 21(12):2250-6 (2010).
Rethore et al., Use of templates to fabricate nanoscale spherical structures for defined architectural control, Small, 6(4):488-98 (2010).
Sadauskas et al., Protracted elimination of gold nanoparticles from mouse liver, Nanomedicine, 5(2):162-9 (2009).
Sharma et al., Characterization of MRI contrast agent-loaded polymeric nanocapsules as versatile vehicle for targeted imaging, Contrast Media Mol. Imaging, 5(2):59-69 (2010).
Shu et al., Gradient cross-linked biodegradable polyelectrolyte nanocapsules for intracellular protein drug delivery, Biomaterials, 31(23):6039-49 (2010).
Skwarczynski et al., Paclitaxel prodrugs: toward smarter delivery of anticancer agents, J. Med. Chem., 49(25):7253-69 (2006).
Storz et al., An abundance of RNA regulators, Annu. Rev. Biochem., 74:199-217 (2005).
Sugihara et al., One-pot synthesis of biomimetic shell cross-linked micelles and nanocages by ATRP in alcohol/water mixtures, Angew. Chem. Int. Ed. Engl., 48(20):3500-3 (2010).
Tan et al., Facile synthesis of hybrid silica nanocapsules by interfacial templating condensation and their application in fluorescence imaging, Chem. Commun. (Camb.), Nov. 7(41):6240-2 (2009).
Turner et al., Nanoscale Cage-like Structures Derived from Polyisoprene-Containing Shell Cross-linked Nanoparticle Templates, Nano Lett., 4(4):683-8 (2004).
Wikipedia entry on Aspirin, Last modified on Oct. 6, 2010 (online). Retrieved on Oct. 7, 2010). Retrieved from the Internet: <URL: http://en.wikipedia.org/wiki/Aspirin>.

(56) References Cited

OTHER PUBLICATIONS

Wikipedia entry on Phenylbutazone. Last modified on Sep. 20, 2010. Online. (Retrieved on Oct. 7, 2010). Retrieved from the Internet: <URL:http://en.wikipedia.org/wiki/Phenylbutazone>.

Wikipedia entry on Warfarin. Last modified on Oct. 5, 2010. (Online) (Retrieved on Oct. 8, 2010). Retrieved from the Internet: <URL:http://en.wikpedia.org/wiki/Warfarin>.

Zhang et al., A novel paclitaxel-loaded poly(epsilon-caprolactone)/Poloxamer 188 blend nanoparticle overcoming multidrug resistance for cancer treatment, Acta Biomater., 6(6):2045-52 (2010).

Zhang et al., Cationic shell-crosslinked knedel-like nanoparticles for highly efficient gene and oligonucleotide transfection of mammalian cells, Biomaterials, 30(5):968-77 (2009).

Zhang et al., Self-assembled monolayers of terminal alkynes on gold, J. Am. Chem. Soc., 129(16):4876-7 (2007).

Zhao et al., A rapid bioassay for single bacterial cell quantitation using bioconjugated nanoparticles, Proc. Natl. Acad. Sci. USA, 101 (42):15027-32 (2004).

First Office Action, Chinese patent application No. 200980146985.6, issue date Oct. 25, 2012.

\* cited by examiner

POLYVALENT RNA-NANOPARTICLE COMPOSITIONS

CROSS-REFERENCE TO RELATED APPLICATIONS

This application claims priority benefit under 35 U.S.C. §119(e) of Provisional U.S. Patent Application No. 61/117,449, filed Nov. 24, 2008, the disclosure of which is incorporated herein by reference in its entirety.

STATEMENT OF GOVERNMENT INTEREST

This invention was made with government support under Grant Number 5U54 CA119341 awarded by the National Institutes of Health, National Cancer Institute/Centers of Cancer Nanotechnology Excellence (NCI/CCNE) and Grant Number 5DP1 OD000285 awarded by the National Institutes of Health (NIH). The government has certain rights in the invention.

FIELD OF THE INVENTION

The present invention concerns nanoparticles functionalized with duplex RNA. The invention also provides a method for conjugating RNA to a nanoparticle.

BACKGROUND OF THE INVENTION

RNA interference (RNAi) is a phenomenon wherein double-stranded RNA (dsRNA), when present in a cell, inhibits expression of a gene that has a sufficiently complementary sequence to a single strand in the double-stranded RNA. Inhibition of gene expression is caused by degradation of messenger RNA (mRNA) transcribed from the target gene [Sharp et al., Genes and Development 15: 485-490 (2001)]. The double-stranded RNA responsible for inducing RNAi is termed interfering RNA. The mechanism and cellular machinery through which dsRNA mediates RNAi has been investigated using both genetic and biochemical approaches. Biochemical analyses suggest that dsRNA introduced into the cytoplasm of a cell is first processed into RNA fragments 21-25 nucleotides long [Hammond et al., Nature 404: 293-296 (2000); Hamilton et al., Science 286: 950-952 (1999); Zamore et al., Cell 101: 25-33 (2000); Yang et al., Current Biology 10: 1191-1200 (2000); Parrish et al., Molecular Cell 6: 1077-1087 (2000)]. It has been shown in in vitro studies that these dsRNAs, termed small interfering RNAs (siRNA) are generated at least in one mechanism by the RNAse III-like enzyme Dicer [Hammond et al., Nature 404: 293-296 (2000)]. These siRNAs likely act as guides for mRNA cleavage, as the target mRNA is cleaved at a position in the center of the region hybridized to a particular siRNA [Sharp 2001]. Biochemical evidence suggests that the siRNA is part of a multicomponent nuclease complex termed the RNA-induced silencing complex (RISC) [Hammond et al., Nature 404: 293-296 (2000)]. One of the proteins of this complex, Argonaute2, has been identified as a product of the argonaute gene family [Sharp et al., Genes and Development 15: 485-490 (2001);]. This protein is essential for mouse development, and cells lacking Argonaute2 are unable to mount an experimental response to siRNAs. Mutations within a cryptic ribonuclease H domain within Argonaute2, as identified by comparison with the structure of an archeal Argonaute protein, inactivate RISC. Thus, Argonaute contributes "Slicer" activity to RISC, providing the catalytic engine for RNAi [Liu et al., Science 305(5689): 1437-1441 (2004)]. This gene family, which also contains the *C. elegans* homolog rde-1 and related genes, the *N. crassa* homolog qde-2, and the *Arabidopsis* homolog arg-1, has been shown to be required for RNAi through genetic studies [Sharp et al., Genes and Development 15: 485-490 (2001); Hammond et al., Nature 404: 293-296 (2000); Hamilton et al., Science 286: 950-952 (1999)]. Genetic screens in *C. elegans* have also identified the mut-7 gene as essential for RNAi. This gene bears resemblance to RNAse D, suggesting that its gene product acts in the mRNA degradation step of the reaction [Sharp et al., Genes and Development 15: 485-490 (2001)].

Over the past decade, researchers have designed, synthesized, studied, and applied polyvalent DNA-functionalized gold nanoparticles (DNA-Au NPs). [Mirkin et al., Nature 382: 607 (1996)]. These efforts have resulted in a new fundamental understanding of hybrid nanostructures [Demers et al., Anal. Chem. 72: 5535 (2000); Jin et al., J. Am. Chem. Soc. 125: 1643 (2003); Lytton-Jean et al., J. Am. Chem Soc 127: 12754-12754 (2005); Storhoff et al., J. Am. Chem. Soc. 122: 4640 (2000); You et al., Soft Matter 2: 190 (2006); Wang et al., Nanomed. 1: 413 (2006)], important and in certain cases commercially viable detection and diagnostic assays [Nam et al., Science 301: 1884 (2003); Stoeva et al., J. Am. Chem. Soc. 128: 8378 (2006); Liu et al., J. Am. Chem. Soc. 126: 12298 (2004); Faulds et al., Anal. Chem. 76: 412 (2004)], and the ability to program materials assembly through the use of DNA synthons [Mirkin et al., Nature 382: 607 (1996); Park et al., Nature 451: 553 (2008); Nykypanchuk et al., Nature, 451: 549 (2008)]. Polyvalent DNA-Au NPs have several unique properties, such as sharp and elevated melting temperatures [Jin et al., J. Am. Chem. Soc. 125: 1643 (2003)], enhanced binding properties [Lytton-Jean et al., J. Am. Chem Soc 127: 12754-12754 (2005)] (as compared with free strands of the same sequence) and distance-dependent optical properties [Elghanian et al., Science 277: 1078 (1997)]. In agreement with research on polyvalent molecular systems [Gestwicki et al., J. Am. Chem. Soc. 124: 14922 (2002)], the high surface DNA density and the ability of the nanoparticles to engage in multidentate interactions are the proposed origin of these unique properties.

SUMMARY OF THE INVENTION

Described herein is a nanoparticle composition that has an associated RNA monolayer imparting physical properties such that the composition is useful for genetic regulation. In contrast to other materials for introducing RNA to a cell, these compositions are not simply a delivery tool for RNA, but rather single entity agents that take advantage of the cooperative properties that result from the arrangement and high density of the surface ligands. The composition described herein enters cells without transfection agents and is resistant to degradation in a manner that enhances knockdown activity compared to conventional polymer carriers.

Thus, in some aspects a nanoparticle composition is provided comprising one or more ribonucleic acid (RNA) polynucleotides in association with a nanoparticle, wherein the RNA polynucleotide has a polypeptide interaction site, and wherein the RNA polynucleotide has a sequence that forms a duplex under conditions appropriate to form the duplex, the duplex having at least one domain in a single strand of the duplex sufficiently complementary to a sequence in a target polynucleotide to permit hybridization of the single strand to the target polynucleotide under appropriate conditions, and hybridization of the domain of the duplex to the sequence in the target polynucleotide creates a substrate site recognized by a polypeptide, and the RNA polynucleotide associated with the nanoparticle is in an orientation specific manner with respect to the polypeptide interaction site and the nanoparticle.

In some aspects a nanoparticle composition is provided in which the RNA polynucleotide is covalently associated with the nanoparticle. In other aspects, a nanoparticle composition is provided in which the RNA polynucleotide is not in covalent association with the nanoparticle.

In further aspects, a nanoparticle composition is provided wherein each RNA polynucleotide in association with the nanoparticle has an identical sequence. In other aspects, a nanoparticle composition is provided wherein at least two RNA polynucleotides in association with the nanoparticle have different sequences.

In some embodiments, a nanoparticle composition is provided wherein the duplex comprises a hairpin structure formed by the RNA polynucleotide.

The methods disclosed herein contemplate a nanoparticle composition further comprising an additional polynucleotide, the additional polynucleotide having a sequence sufficiently complementary to a sequence in the RNA polynucleotide to permit hybridization to the RNA polynucleotide under appropriate conditions to form the duplex.

In some aspects, a nanoparticle composition is provided wherein the additional polynucleotide is RNA. In other aspects, a nanoparticle composition is provided wherein the additional polynucleotide is deoxyribonucleic acid (DNA).

In further embodiments, a nanoparticle composition is provided wherein the additional polynucleotide is covalently associated with the nanoparticle. In some aspects, a nanoparticle composition is provided wherein the additional polynucleotide is not covalently associated with the nanoparticle.

In some embodiments, a nanoparticle composition is provided wherein the polypeptide interaction site is located proximal to the nanoparticle with respect to a midpoint in the RNA polynucleotide.

In further embodiments, a nanoparticle composition is provided wherein the polypeptide interaction site is located distal to the nanoparticle with respect to a midpoint in the RNA polynucleotide.

In some aspects of the methods, a nanoparticle composition is provided having surface density of the RNA of at least about 2 pmol/cm$^2$ to about 1000 pmol/cm$^2$.

In various embodiments, a nanoparticle composition is provided wherein the polypeptide interaction site associates with a protein selected from the group consisting of RNase H, RNase D, RNase L, RNase III, Dicer, Argonaute, Argonaute2, and human immunodeficiency virus transactivating response RNA-binding protein (TRBP).

Further aspects of the methods provide a nanoparticle composition wherein the domain of the polynucleotide is about 10 nucleotides in length.

In some embodiments, a nanoparticle composition is provided wherein the RNA polynucleotide further includes a second domain sufficiently complementary to a second sequence in the target polynucleotide and hybridization of the second domain of the RNA polynucleotide to the second sequence in the target polynucleotide creates an additional substrate site recognized by a second polypeptide. In some aspects, a nanoparticle composition is provided wherein the second domain of the polynucleotide is about 10 nucleotides in length.

In some aspects, a nanoparticle composition is provided wherein the substrate site and the additional substrate site are the same. In other aspects, a nanoparticle composition is provided wherein the substrate site and the additional substrate site are different.

A nanoparticle composition is provided in some aspects wherein the RNA polynucleotide and the additional polynucleotide are complementary to each other over a length sufficient to allow hybridization. In other aspects, a nanoparticle composition is provided wherein the RNA polynucleotide and the additional polynucleotide are complementary to each other over their entire length.

In some embodiments, a nanoparticle composition is provided wherein the RNA polynucleotide is conjugated to the nanoparticle through a thiol linkage.

In some aspects, a nanoparticle composition is provided wherein the RNA polynucleotide has a half-life that is at least substantially the same as a half-life of identical RNA polynucleotide that is not associated with a nanoparticle. In other aspects, a nanoparticle composition is provided wherein the RNA polynucleotide has a half-life that is about 1-fold greater, about 2-fold greater, about 3-fold greater, about 4-fold greater, about 5-fold greater or more than a half-life of identical RNA that is not associated with a nanoparticle.

In various embodiments, a nanoparticle composition is provided wherein the RNA polynucleotide is about 5 to about 100 nucleotides in length. In some aspects, a nanoparticle composition is provided wherein the additional polynucleotide is about 5 to about 100 nucleotides in length.

In some embodiments, a nanoparticle composition is provided in which the nanoparticle is gold. In some aspects, a nanoparticle composition is provided in which the nanoparticle is silver.

In some aspects, a method of associating a RNA polynucleotide to a nanoparticle is provided comprising the step of aging a mixture of a thiolated RNA polynucleotide duplex with the nanoparticle in a series of solutions to associate the RNA polynucleotide to the nanoparticle, each solution comprising an increasing concentration of sodium chloride (NaCl) relative to a previous solution beginning with a first solution comprising about 0.1 M NaCl. In related aspects, the method further comprises the step of sonicating the mixture after the last aging step. In some aspects, the method further comprises the step of isolating the nanoparticles.

In some embodiments, a method of associating a RNA to a nanoparticle is provided comprising:
(a) mixing a thiolated RNA duplex with the nanoparticle in a solution comprising about 0.1 M sodium chloride (NaCl);
(b) aging the mixture in a series of salt solutions, each comprising an increasing concentration of NaCl relative to a previous solution;
(c) sonicating the mixture; and
(d) purifying the conjugated nanoparticle.

In various aspects of the method, the series of salt solutions ranges from about 0.1 M to about 0.3 M NaCl.

Some aspects of the method further comprise passivating the surface of the nanoparticle with oligo(ethylene glycol) thiol (OEG).

In some embodiments, a method of regulating expression of a target polynucleotide is provided comprising the step of hybridizing the target polynucleotide with the domain of a nanoparticle composition of the disclosure to form a substrate site for a polypeptide. In some aspects, the hybridizing results in degradation of the target polynucleotide. In various aspects, the polypeptide is selected from the group consisting of RNase H, RNase D, RNase L, RNase III, Dicer, Argonaute, Argonaute2, and TRBP.

Further aspects of the invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

Figure 1:
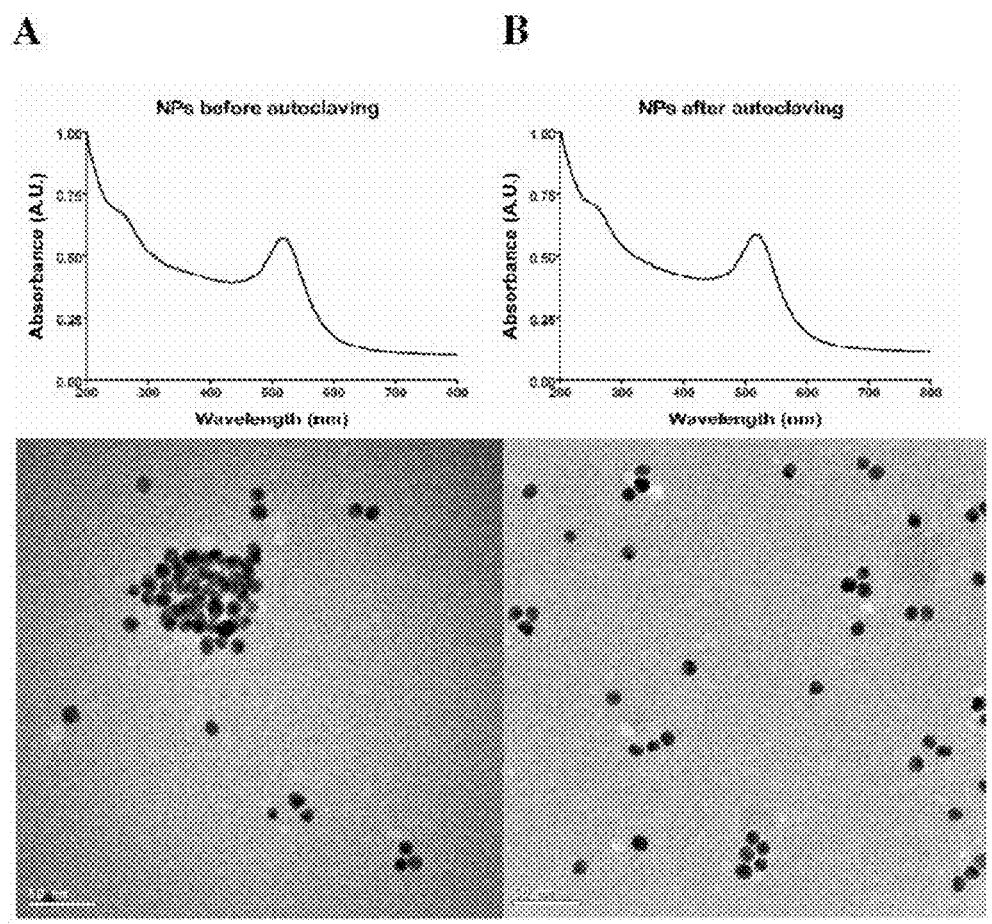
FIG. 1 depicts the characterization of gold nanoparticles (NPs). Nanoparticle absorbance spectra and TEM imaging before (a) and after (b) autoclaving. Scale bar is 50 nm.

To date, no methods have been developed for utilizing polyvalent particles and their unusual properties to load and transport RNA across cell membranes. Indeed, one must develop synthetic routes and materials that overcome one of the most challenging problems associated with RNA, most notably its chemical instability.

The ability to specifically inhibit expression of a target gene by RNAi has obvious benefits. For example, many diseases arise from the abnormal expression of a particular gene or group of genes. RNAi could be used to inhibit the expression of the deleterious gene and therefore alleviate symptoms of a disease or even provide a cure. For example, genes contributing to a cancerous state or to viral replication could be inhibited. In addition, mutant genes causing dominant genetic diseases such as myotonic dystrophy could be inhibited. Inflammatory diseases such as arthritis could also be treated by inhibiting such genes as cyclooxygenase or cytokines. Examples of targeted organs would include without limitation the liver, pancreas, spleen, skin, brain, prostate, heart etc. In addition, RNAi could be used to generate animals that mimic true genetic "knockout" animals to study gene function. Further description of contemplated uses and targets is provided below.

Drug discovery could also be facilitated by RNA technology. The RNA approach for target validation provides a quicker and less expensive approach to screen potential drug targets. Information for drug targeting is gained not only by inhibiting a potential drug target but also by determining whether an inhibited protein, and therefore the pathway, has significant phenotypic effects. For example, inhibition of LDL receptor expression should raise plasma LDL levels and, therefore, suggest that up-regulation of the receptor would be of therapeutic benefit. Expression arrays can be used to determine the responsive effect of inhibition on the expression of genes other than the targeted gene or pathway [Sharp et al., Genes and Development 15: 485-490 (2001)]. It will place the gene product within functional pathways and networks (interacting pathways).

It is disclosed herein that gold nanoparticles functionalized with RNA oligonucleotides take advantage of the ensemble properties that result from the surface functionalization of oligonucleotides, to increase the stability and efficacy of the bound RNA, while retaining the ability to act in the catalytic RNA interference pathway.

The synthesis of polyvalent RNA-nanoparticle compositions (RNA-Au NPs for those aspects wherein the nanoparticle is gold) requires that all components are free of nucleases, such as RNase, which degrades RNA ligands and results in unstable Au NP interactions by exposing the Au surface (as evidenced by aggregation). While conditions for preparing RNase free organic components and solutions are well established, provided herein are methods for creating RNase free inorganic gold nanoparticles.

It is to be noted that the terms "polynucleotide" and "oligonucleotide" are used interchangeably herein. It is also to be noted that the terms "conjugated" and "functionalized" are also used interchangeably herein.

As used herein, a "substrate site" is a location on a polynucleotide (which is single- or double-stranded) that is recognized and acted upon by a polypeptide. As used herein, "acted upon" is understood to mean any enzymatic function performed by a polypeptide that recognizes and binds to the substrate site.

As used herein, a "polypeptide interaction site" refers to a site on a polynucleotide (which is single- or double-stranded) that is recognized by a polypeptide. Recognition of the interaction site by a polypeptide, in various aspects, results in cleavage of the polynucleotide. In certain embodiments, the polypeptide itself that recognizes the polypeptide interaction site acts on the polynucleotide and in other embodiments, the polypeptide that recognizes the polynucleotide recognition site directs activity of one or more additional polypeptides to act on the polynucleotide.

As used herein, the term "target" or "target polynucleotide" refers to a polynucleotide against which a given RNA polynucleotide can be directed.

As used herein, "RNA" refers to a molecule comprising at least one ribonucleotide residue.

As used herein, "duplex" refers to a region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex" has 19 base pairs. The remaining bases may, for example, exist as 5' and 3' overhangs. Further, within the duplex, 100% complementarity is not required; substantial complementarity is allowable within a duplex. Substantial complementarity refers to 75% or greater complementarity. For example, a mismatch in a duplex consisting of 19 base pairs results in 94.7% complementarity, rendering the duplex substantially complementary.

Nanoparticles

Nanoparticles are thus provided which are functionalized to have a polynucleotide attached thereto. The size, shape and chemical composition of the nanoparticles contribute to the properties of the resulting polynucleotide-functionalized nanoparticle. These properties include for example, optical properties, optoelectronic properties, electrochemical properties, electronic properties, stability in various solutions, magnetic properties, and pore and channel size variation. Mixtures of nanoparticles having different sizes, shapes and/or chemical compositions, as well as the use of nanoparticles having uniform sizes, shapes and chemical composition, and therefore a mixture of properties are contemplated. Examples of suitable particles include, without limitation, aggregate particles, isotropic (such as spherical particles), anisotropic particles (such as non-spherical rods, tetrahedral, and/or prisms) and core-shell particles, such as those described in U.S. Pat. No. 7,238,472 and International Publication No. WO 2003/08539, the disclosures of which are incorporated by reference in their entirety.

In one embodiment, the nanoparticle is metallic, and in various aspects, the nanoparticle is a colloidal metal. Thus, in various embodiments, nanoparticles of the invention include metal (including for example and without limitation, silver, gold, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials.

Also, as described in U.S. Patent Publication No 2003/0147966, nanoparticles of the invention include those that are available commercially, as well as those that are synthesized, e.g., produced from progressive nucleation in solution (e.g., by colloid reaction) or by various physical and chemical vapor deposition processes, such as sputter deposition. See, e.g., HaVashi, Vac. Sci. Technol. A5(4):1375-84 (1987); Hayashi, Physics Today, 44-60 (1987); MRS Bulletin, January 1990, 16-47. As further described in U.S. Patent Publication No 2003/0147966, nanoparticles contemplated are alternatively produced using $HAuCl_4$ and a citrate-reducing agent, using methods known in the art. See, e.g., Marinakos et al., Adv. Mater. 11:34-37(1999); Marinakos et al., Chem. Mater. 10: 1214-19(1998); Enustun & Turkevich, J. Am. Chem. Soc. 85: 3317(1963).

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be derivatized as described herein.

Polynucleotide Attachment to a Nanoparticle

Nanoparticles with polynucleotides attached thereto are thus provided wherein a duplex RNA is associated with the nanoparticle. In some aspects, the RNA that is associated with a nanoparticle is a small interfering RNA (siRNA). Association of the duplex RNA to the nanoparticles is contemplated through various means.

According to methods described herein, citrate-stabilized gold nanoparticles are synthesized and the particles are treated with 0.1% diethylpyrocarbonate (DEPC) for 12 hours with stirring, then autoclaved at 121° C. for 60 minutes. In some aspects, treatment of the nanoparticles with DEPC is performed for about 1 hour. In various aspects, treatment of the nanoparticles with DEPC is performed for about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 20, about 25, about 30, about 3 days, about 7 days or more.

In one embodiment, a single strand RNA polynucleotide is attached directly to the nanoparticle, optionally through a spacer as described herein, In those aspects where a single strand RNA polynucleotide is attached to the nanoparticle, the RNA polynucleotide comprises two portions that are sufficiently complementary to allow the two portions to hybridize to each other under appropriate conditions to form a hairpin structure.

In another embodiment, a duplex RNA is immobilized directly on a nanoparticle, optionally through a spacer as described herein, such that only one strand of the duplex RNA is attached directly to the nanoparticle.

In other embodiments, the polynucleotide attached to a nanoparticle is DNA. When DNA is attached to the nanoparticle, the DNA is comprised of a sequence that is sufficiently complementary to a single strand region of a RNA duplex such that hybridization of the DNA polynucleotide attached to a nanoparticle and the single strand region of the RNA duplex takes place, thereby associating the duplex RNA to the nanoparticle. In one aspect, the single strand region of the duplex RNA is an overhanging end. The DNA in various aspects is single stranded or double-stranded, as long as the double-stranded molecule also include a single strand region that hybridizes to the single strand region of the duplex RNA.

Polynucleotide Orientation

Sense vs. Antisense

In some aspects, the strand of RNA that is attached to the nanoparticle is the "sense" strand and the complementary strand of the duplex RNA is hybridized to the sense strand but is not attached to the nanoparticle. In other aspects, the strand of RNA that is attached to the nanoparticle is the "antisense" strand, and the complementary strand of the duplex RNA is hybridized to the antisense strand but is not attached to the nanoparticle. As used herein, a "sense" strand is a strand that is identical to a target polynucleotide and an "antisense" strand is a strand that is complementary to a target polynucleotide. Attachment of the sense strand or the antisense strand to the nanoparticle determines one aspect of the orientation of the double-stranded RNA to the nanoparticle.

It is demonstrated herein that a RNA duplex wherein the sense strand is attached to a nanoparticle and an antisense strand is hybridized to the sense strand but is not attached to a nanoparticle has higher activity (see Example 5) than a RNA duplex in which the antisense strand is attached to a nanoparticle and the sense strand is hybridized to the antisense strand but is not attached to the nanoparticle. Without being bound by theory, the orientation of the attachment of a RNA duplex to a nanoparticle (for example and without limitation, whether a sense strand or an antisense strand of a RNA duplex is attached to a nanoparticle) is contemplated to be important for presenting a substrate for a polypeptide contemplated by the present disclosure. In some aspects, the polypeptide is Dicer. In some aspects, the polypeptide is Argonaute.

Position of Polypeptide Interaction Site

In some embodiments, the disclosure contemplates that a polynucleotide attached to a nanoparticle is RNA. It is also contemplated that a polynucleotide is attached to a nanoparticle such that a protein interaction site located in a sequence in the RNA is either proximal or distal relative to the nanoparticle. In these aspects, "proximal" and "distal" refer to a midpoint on the polynucleotide. For example, if a polynucleotide that is attached to a nanoparticle is 20 bases in length, then the midpoint is at a location 10 bases from the nanoparticle, and a protein interaction site can either be proximal or distal relative to the tenth base.

Immobilizing a RNA polynucleotide on a nanoparticle using methods described herein allows for the control of access to the duplex by a polypeptide of the disclosure.

In some embodiments, spacer sequences of varying length are utilized to vary the number of and the distance between the RNA polynucleotides on a nanoparticle thus controlling the rates of target polynucleotide degradation. Without being bound by theory, one can control the rate of target polynucleotide degradation by immobilizing a RNA polynucleotide on a nanoparticle such that the protein interaction site is in a proximal position as described above. This aspect, combined with a surface density aspect as described below, can allow or prevent access by a polypeptide of the disclosure to the protein interaction site.

Spacers are described in further detail herein below.

Spacers

In certain aspects, functionalized nanoparticles are contemplated which include those wherein an oligonucleotide is attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotide in tandem, whether the oligonucleotides have the same sequence or have different sequences. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, an ethylglycol, or combinations thereof.

In certain aspects, the spacer has a polynucleotide covalently bound to it which can bind to the nanoparticles. These polynucleotides are the same polynucleotides as described above. As a result of the binding of the spacer to the nanoparticles, the polynucleotide is spaced away from the surface of the nanoparticles and is more accessible for hybridization with its target. In instances wherein the spacer is a polynucleotide, the length of the spacer in various embodiments at least about 10 nucleotides, 10-30 nucleotides, or even greater than 30 nucleotides. The spacer may have any sequence which does not interfere with the ability of the polynucleotides to become bound to the nanoparticles or to the target polynucleotide. The spacers should not have sequences complementary to each other or to that of the oligonucleotides, but may be all or in part complementary to the target polynucleotide. In certain aspects, the bases of the polynucleotide spacer are all adenines, all thymines, all cytidines, all guanines, all uracils, or all some other modified base.

Surface Density

Nanoparticles as provided herein have a packing density of the polynucleotides on the surface of the nanoparticle that is, in various aspects, sufficient to result in cooperative behavior between nanoparticles and between polynucleotide strands on a single nanoparticle. In another aspect, the cooperative behavior between the nanoparticles increases the resistance of the polynucleotide to nuclease degradation. In yet another aspect, the uptake of nanoparticles by a cell is influenced by the density of polynucleotides associated with the nanoparticle. As described in PCT/US2008/65366, incorporated herein by reference in its entirety, a higher density of polynucleotides on the surface of a nanoparticle is associated with an increased uptake of nanoparticles by a cell.

A surface density adequate to make the nanoparticles stable and the conditions necessary to obtain it for a desired combination of nanoparticles and polynucleotides can be determined empirically. Generally, a surface density of at least 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Density of polynucleotides on the surface of a nanoparticle has been shown to modulate specific polypeptide interactions with the polynucleotide on the surface and/or with the nanoparticle itself. Under various conditions, some polypeptides may be prohibited from interacting with polynucleotides associated with a nanoparticle based on steric hindrance caused by the density of polynucleotides. In aspects where interaction of polynucleotides with polypeptides that are otherwise precludes by steric hindrance is desirable, the density of polynucleotides on the nanoparticle surface is decreased to allow the polypeptide to interact with the polynucleotide.

Polynucleotide surface density has also been shown to modulate stability of the polynucleotide associated with the nanoparticle. In one embodiment, an RNA polynucleotide associated with a nanoparticle is provided wherein the RNA polynucleotide has a half-life that is at least substantially the same as the half-life of an identical RNA polynucleotide that is not associated with a nanoparticle. In other embodiments, the RNA polynucleotide associated with the nanoparticle has a half-life that is about 5% greater, about 10% greater, about 20% greater, about 30% greater, about 40% greater, about 50% greater, about 60% greater, about 70% greater, about 80% greater, about 90% greater, about 2-fold greater, about 3-fold greater, about 4-fold greater, about 5-fold greater, about 6-fold greater, about 7-fold greater, about 8-fold greater, about 9-fold greater, about 10-fold greater, about 20-fold greater, about 30-fold greater, about 40-fold greater, about 50-fold greater, about 60-fold greater, about 70-fold greater, about 80-fold greater, about 90-fold greater, about 100-fold greater, about 200-fold greater, about 300-fold greater, about 400-fold greater, about 500-fold greater, about 600-fold greater, about 700-fold greater, about 800-fold greater, about 900-fold greater, about 1000-fold greater, about 5000-fold greater, about 10,000-fold greater, about 50,000-fold greater, about 100,000-fold greater, about 200,000-fold greater, about 300,000-fold greater, about 400,000-fold greater, about 500,000-fold greater, about 600,000-fold greater, about 700,000-fold greater, about 800,000-fold greater, about 900,000-fold greater, about 1,000,000-fold greater or more than the half-life of an identical RNA polynucleotide that is not associated with a nanoparticle.

Methods of Attaching Polynucleotides

Polynucleotides contemplated for use in the methods include those bound to the nanoparticle through any means. Regardless of the means by which the polynucleotide is attached to the nanoparticle, attachment in various aspects is effected through a 5' linkage, a 3' linkage, some type of internal linkage, or any combination of these attachments.

In one aspect, the nanoparticles, the polynucleotides or both are functionalized in order to attach the polynucleotides to the nanoparticles. Methods to functionalize nanoparticles and polynucleotides are known in the art. For instance, polynucleotides functionalized with alkanethiols at their 3'-termini or 5'-termini readily attach to gold nanoparticles. See Whitesides, Proceedings of the Robert A. Welch Foundation 39th Conference On Chemical Research Nanophase Chemistry, Houston, Tex., pages 109-121 (1995). See also, Mucic et al. [Chem. Commun. 555-557 (1996)] which describes a method of attaching 3' thiol DNA to flat gold surfaces. The alkanethiol method can also be used to attach oligonucleotides to other metal, semiconductor and magnetic colloids and to the other types of nanoparticles described herein. Other functional groups for attaching oligonucleotides to solid surfaces include phosphorothioate groups (see, for example, U.S. Pat. No. 5,472,881 for the binding of oligonucleotide-phosphorothioates to gold surfaces), substituted alkylsiloxanes [(see, for example, Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., [Anal. Chem., 67, 735-743] for binding of aminoalkylsiloxanes and for similar binding of mercaptoaklylsiloxanes]. Polynucleotides with a 5' thionucleoside or a 3' thionucleoside may also be used for attaching oligonucleotides to solid surfaces. The following references describe other methods which may be employed to attached oligonucleotides to nanoparticles: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

U.S. patent application Ser. Nos. 09/760,500 and 09/820,279 and international application nos. PCT/US01/01190 and PCT/US01/10071 describe oligonucleotides functionalized with a cyclic disulfide. The cyclic disulfides in certain aspects have 5 or 6 atoms in their rings, including the two sulfur atoms. Suitable cyclic disulfides are available commercially or are synthesized by known procedures. Functionalization with the reduced forms of the cyclic disulfides is also contemplated. Functionalization with triple cyclic disulfide anchoring groups are described in PCT/US2008/63441, incorporated herein by reference in its entirety.

In certain aspects wherein cyclic disulfide functionalization is utilized, oligonucleotides are attached to a nanoparticle through one or more linkers. In one embodiment, the linker comprises a hydrocarbon moiety attached to a cyclic disulfide. Suitable hydrocarbons are available commercially, and are attached to the cyclic disulfides. The hydrocarbon moiety is, in one aspect, a steroid residue. Oligonucleotide-nanoparticle compositions prepared using linkers comprising a steroid residue attached to a cyclic disulfide are more stable compared to compositions prepared using alkanethiols or acyclic disulfides as the linker, and in certain instances, the oligonucleotide-nanoparticle compositions have been found to be 300 times more stable. In certain embodiments the two sulfur atoms of the cyclic disulfide are close enough together so that both of the sulfur atoms attach simultaneously to the nanoparticle. In other aspects, the two sulfur atoms are adjacent each other. In aspects where utilized, the hydrocarbon moiety is large enough to present a hydrophobic surface screening the surfaces of the nanoparticle.

In other aspects, a method for attaching oligonucleotides onto a surface is based on an aging process described in U.S. application Ser. No. 09/344,667, filed Jun. 25, 1999; Ser. No.

09/603,830, filed Jun. 26, 2000; Ser. No. 09/760,500, filed Jan. 12, 2001; Ser. No. 09/820,279, filed Mar. 28, 2001; Ser. No. 09/927,777, filed Aug. 10, 2001; and in International application nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures which are incorporated by reference in their entirety. The aging process provides nanoparticle-oligonucleotide compositions with enhanced stability and selectivity. The process comprises providing oligonucleotides, in one aspect, having covalently bound thereto a moiety comprising a functional group which can bind to the nanoparticles. The moieties and functional groups are those that allow for binding (i.e., by chemisorption or covalent bonding) of the oligonucleotides to nanoparticles. For example, oligonucleotides having an alkanethiol, an alkanedisulfide or a cyclic disulfide covalently bound to their 5' or 3' ends bind the oligonucleotides to a variety of nanoparticles, including gold nanoparticles.

Compositions produced by use of the "aging" step have been found to be considerably more stable than those produced without the "aging" step. Increased density of the oligonucleotides on the surfaces of the nanoparticles is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically. Generally, a surface density of at least 2 picomoles/$cm^2$ will be adequate to provide stable nanoparticle-oligonucleotide compositions. Regardless, various oligonucleotide densities are contemplated as disclosed herein.

An "aging" step is incorporated into production of functionalized nanoparticles following an initial binding or oligonucleotides to a nanoparticle. In brief, the oligonucleotides are contacted with the nanoparticles in water for a time sufficient to allow at least some of the oligonucleotides to bind to the nanoparticles by means of the functional groups. Such times can be determined empirically. In one aspect, a time of about 12-24 hours is contemplated. Other suitable conditions for binding of the oligonucleotides can also be determined empirically. For example, a concentration of about 10-20 nM nanoparticles and incubation at room temperature is contemplated.

Next, at least one salt is added to the water to form a salt solution. The salt is any water-soluble salt, including, for example and without limitation, sodium chloride, magnesium chloride, potassium chloride, ammonium chloride, sodium acetate, ammonium acetate, a combination of two or more of these salts, or one of these salts in phosphate buffer. The salt is added as a concentrated solution, or in the alternative as a solid. In various embodiments, the salt is added all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the oligonucleotides from each other and, either the electrostatic attraction of the negatively-charged oligonucleotides for positively-charged nanoparticles, or the electrostatic repulsion of the negatively-charged oligonucleotides from negatively-charged nanoparticles. Gradually reducing the electrostatic attraction and repulsion by adding the salt gradually over time gives the highest surface density of oligonucleotides on the nanoparticles. Suitable ionic strengths can be determined empirically for each salt or combination of salts. In one aspect, a final concentration of sodium chloride of from about 0.01 M to about 1.0 M in phosphate buffer is utilized, with the concentration of sodium chloride being increased gradually over time. In another aspect, a final concentration of sodium chloride of from about 0.01 M to about 0.5 M, or about 0.1 M to about 0.3 M is utilized, with the concentration of sodium chloride being increased gradually over time.

After adding the salt, the oligonucleotides and nanoparticles are incubated in the salt solution for a period of time to allow additional oligonucleotides to bind to the nanoparticles to produce the stable nanoparticle-oligonucleotide compositions. An increased surface density of the oligonucleotides on the nanoparticles stabilizes the compositions, as has been described herein. The time of this incubation can be determined empirically. By way of example, in one aspect a total incubation time of about 24-48, wherein the salt concentration is increased gradually over this total time, is contemplated. This second period of incubation in the salt solution is referred to herein as the "aging" step. Other suitable conditions for this "aging" step can also be determined empirically. By way of example, an aging step is carried out with incubation at room temperature and pH 7.0.

The compositions produced by use of the "aging" are in general more stable than those produced without the "aging" step. As noted above, this increased stability is due to the increased density of the oligonucleotides on the surfaces of the nanoparticles which is achieved by the "aging" step. The surface density achieved by the "aging" step will depend on the size and type of nanoparticles and on the length, sequence and concentration of the oligonucleotides.

As used herein, "stable" means that, for a period of at least six months after the compositions are made, a majority of the oligonucleotides remain attached to the nanoparticles and the oligonucleotides are able to hybridize with nucleic acid and oligonucleotide targets under standard conditions encountered in methods of detecting nucleic acid and methods of nanofabrication.

Polynucleotides

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Nanoparticles provided that are functionalized with a polynucleotide, or modified form thereof, generally comprise a polynucleotide from about 5 nucleotides to about 100 nucleotides in length. More specifically, nanoparticles are functionalized with polynucleotide that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Polynucleotides contemplated for attachment to a nanoparticle include those which modulate expression of a gene product expressed from a target polynucleotide. Accordingly, RNA polynucleotides which hybridize to a target polynucleotide and initiate an RNAse activity (for example RNAse H), triple helix forming polynucleotides which hybridize to double-stranded polynucleotides and inhibit transcription, and ribozymes which hybridize to a target polynucleotide and inhibit translation, are contemplated.

In various aspects, if a specific mRNA is targeted, a single nanoparticle-binding agent composition has the ability to bind to multiple copies of the same transcript. In one aspect, a nanoparticle is provided that is functionalized with identical polynucleotides, i.e., each polynucleotide has the same length and the same sequence. In other aspects, the nanoparticle is functionalized with two or more polynucleotides which are not identical, i.e., at least one of the attached polynucleotides differ from at least one other attached polynucleotide in that it has a different length and/or a different sequence. In aspects wherein different polynucleotides are attached to the nanoparticle, these different polynucleotides bind to the same single target polynucleotide but at different locations, or substrate sites, or bind to different target polynucleotides which encode different gene products. Accordingly, in various aspects, a single nanoparticle-binding agent composition target more than one gene product. Polynucleotides are thus target-specific polynucleotides, whether at one or more specific regions in the target polynucleotide, or over the entire length of the target polynucleotide as the need may be to effect a desired level of inhibition of gene expression.

Polynucleotide Features

The present disclosure provides, in various embodiments, polyvalent RNA-nanoparticle compositions that are useful for gene regulation. Small interfering RNAs are double stranded RNA agents that have complementarity to (i.e., are able to hybridize with) a portion of the target RNA (generally messenger RNA (mRNA)). Generally, such complementarity is 100%, but can be less if desired, such as about 20%, about 25%, about 30%, about 35%, about 40%, about 45%, about 50%, about 55%, about 60%, about 70%, about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. For example, 19 bases out of 21 bases may be base-paired. Thus, it will be understood that an oligonucleotide used in the methods need not be 100% complementary to a desired target nucleic acid to be specifically hybridizable. Moreover, oligonucleotides may hybridize to each other over one or more segments such that intervening or adjacent segments are not involved in the hybridization event (e.g., a loop structure or hairpin structure). Percent complementarity between any given oligonucleotide can be determined routinely using BLAST programs (Basic Local Alignment Search Tools) and PowerBLAST programs known in the art (Altschul et al., 1990, J. Mol. Biol., 215: 403-410; Zhang and Madden, 1997, Genome Res., 7: 649-656).

In some aspects, where selection between various allelic variants is desired, 100% complementarity to the target gene is required in order to effectively discern the target sequence from the other allelic sequence. When selecting between allelic targets, choice of length is also an important factor because it is the other factor involved in the percent complementary and the ability to differentiate between allelic differences.

"Hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

The term "RNA" includes duplexes of two separate strands, as well as single, triple, or quadruple stranded structures. An example of a single strand RNA is an RNA with a hairpin loop. The RNA sequence needs to be of sufficient length to bring the small interfering RNA and target RNA together through complementary base-pairing interactions. The RNA useful in the methods disclosed herein may be of varying lengths. The RNA, as disclosed herein, comprises a domain in a single strand of the duplex sufficiently complementary to a sequence in a target polynucleotide to permit hybridization of the single strand to the target polynucleotide under appropriate conditions, and hybridization of the domain of the duplex to the sequence in the target polynucleotide creates a substrate site recognized by a polypeptide. The length of this domain is generally greater than or equal to ten nucleotides and of sufficient length to hybridize with the target RNA; specifically 10-100 nucleotides; more specifically any integer between 10 and 80 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100. By "sufficient length" is meant an oligonucleotide of greater than or equal to 10 nucleotides that is of a length great enough to provide the intended function under the expected condition.

RNA may be polymerized in vitro, recombinant RNA, contain chimeric sequences, or derivatives of these groups. The RNA contains, in various embodiments, ribonucleotides, deoxyribonucleotides, synthetic nucleotides, or any suitable combination such that expression of the target gene is inhibited.

A delivered RNA can stay within the cytoplasm or nucleus. The RNA can be delivered to a cell to inhibit expression an endogenous or exogenous nucleotide sequence or to affect a specific physiological characteristic not naturally associated with the cell.

A RNA can be delivered to a cell in order to produce a cellular change that is therapeutic. The delivery of RNA or other genetic material for therapeutic purposes (the art of improving health in an animal including treatment or prevention of disease) is called gene therapy. The RNA can be delivered either directly to the organism in situ or indirectly by transfer to a cell ex vivo that is then transplanted into the organism. Entry into the cell is required for the RNA to block the production of a protein or to decrease the amount of a RNA. Polynucleotide sequences contemplated by the present disclosure are further described below.

Polynucleotide Sequences and Hybridization

In some aspects, the disclosure provides methods of targeting specific nucleic acids. Any type of nucleic acid may be targeted, and the methods may be used, e.g., for therapeutic modulation of gene expression (See, e.g., PCT/US2006/022325, the disclosure of which is incorporated herein by reference). Examples of nucleic acids that can be targeted by the methods of the invention include but are not limited to genes (e.g., a gene associated with a particular disease), viral RNA, or mRNA, RNA, single-stranded nucleic acids.

The target nucleic acid may be in cells, tissue samples, or biological fluids, as also known in the art. See, e.g., Sambrook et al., Molecular Cloning: A Laboratory Manual (2nd ed. 1989) and B. D. Hames and S. J. Higgins, Eds., Gene Probes 1 (IRL Press, New York, 1995).

The terms "start codon region" and "translation initiation codon region" refer to a portion of a mRNA or gene that encompasses contiguous nucleotides in either direction (i.e., 5' or 3') from a translation initiation codon. Similarly, the terms "stop codon region" and "translation termination codon region" refer to a portion of such a mRNA or gene that encompasses contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligonucleotides on the functionalized nanoparticles.

Other target regions include the 5' untranslated region (5'UTR), the portion of an mRNA in the 5' direction from the translation initiation codon, including nucleotides between the 5' cap site and the translation initiation codon of a mRNA (or corresponding nucleotides on the gene), and the 3' untranslated region (3'UTR), the portion of a mRNA in the 3' direction from the translation termination codon, including nucleotides between the translation termination codon and 3' end of a mRNA (or corresponding nucleotides on the gene). The 5' cap site of a mRNA comprises an N7-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap site.

For prokaryotic target nucleic acid, in various aspects, the nucleic acid is RNA transcribed from genomic DNA. For eukaryotic target nucleic acid, the nucleic acid is an animal nucleic acid, a plant nucleic acid, a fungal nucleic acid, including yeast nucleic acid. As above, the target nucleic acid is a RNA transcribed from a genomic DNA sequence. In certain aspects, the target nucleic acid is a mitochondrial nucleic acid. For viral target nucleic acid, the nucleic acid is viral genomic RNA, or RNA transcribed from viral genomic DNA.

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an oligonucleotide-functionalized nanoparticle. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanoparticle and a specific oligonucleotide.

Modified Polynucleotides

Modified polynucleotides are contemplated for functionalizing nanoparticles wherein both one or more sugar and/or one or more internucleotide linkage of the nucleotide units in the polynucleotide is replaced with "non-naturally occurring" groups. In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714, 331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118, 800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the oligo consists of 2 to 4, desirably 3, groups/atoms selected from —$CH_2$—, —O—, —S—, —NRH—, >C=O, >C=NRH, >C=S, —Si(R")₂—, —SO—, —S(O)₂—, —P(O)₂—, —PO(BH₃)—, —P(O,S)—, —P(S)₂—, —PO(R")—, —PO(OCH₃)—, and —PO(NHRH)—, where RH is selected from hydrogen and C1-4-alkyl, and R" is selected from C1-6-alkyl and phenyl. Illustrative examples of such linkages are —CH₂—CH₂—CH₂—, —CH₂—CO—CH₂—, —CH₂—CHOH—CH₂—, —O—CH2-O—, —O—CH2-CH2-, —O—CH2-CH=(including R5 when used as a linkage to a succeeding monomer), —CH₂—CH₂—O—, —NRH—CH₂—CH₂—, —CH₂—CH₂—NRH—, —CH₂—NRH—CH₂—, —O—CH₂—CH₂—NRH—, —NRH—CO—O—, —NRH—CO—NRH—, —NRH—CS—NRH—, —NRH—C(=NRH)—NRH—, —NRH—CO—CH₂—NRH—O—CO—O—, —O—CO—CH₂—O—, —O—CH₂—CO—O—, —CH₂—CO—NRH—, —O—CO—NRH—, —NRH—CO—CH₂—, —O—CH₂—CO—NRH—, —O—CH₂—CH₂—NRH—, —CH=N—O—, —CH₂—NRH—O—, —CH₂—O—N=(including R5 when used as a linkage to a succeeding monomer), —CH₂—O—NRH—, —CO—NRH—CH₂—, —CH₂—NRH—O—, —CH₂—NRH—CO—, —O—NRH—CH₂—, —O—NRH, —O—CH₂—S—, —S—CH₂—O—, —CH₂—CH₂—S—, —O—CH₂—CH₂—S—, —S—CH₂—CH=(including R5 when used as a linkage to a succeeding monomer), —S—CH₂—CH₂—, —S—CH₂—CH₂—O—, —S—CH₂—CH₂—S—, —CH₂—S—CH₂—, —CH₂SO—CH₂—, —CH₂—SO₂—CH₂—, —O—SO—O—, —O—S(O)₂—O—, —O—S(O)₂—CH₂—, —O—S(O)₂—NRH—, —NRH—S(O)₂—CH₂—; —O—S(O)₂—CH₂—, —O—P(O)₂—O—, —O—P(O,S)—O—, —O—P(S)₂—O—, —S—P(O)₂—O—, —S—P(O,S)—O—, —S—P(S)₂—O—, —O—P(O)₂—S—, —O—P(O,S)—S—, —O—P(S)₂—S—, —S—P(O)₂—S—, —S—P(O,S)—S—, —S—P(S)₂—S—, —O—PO(R")—O—, —O—PO(OCH₃)—O—, —O—PO(OCH₂CH₃)—O—, —O—PO(OCH₂CH₂S—R)—O—, —O—PO(BH₃)—O—, —O—PO(NHRN)—O—, —O—P(O)₂—NRHH—, —NRH—P(O)₂—O—, —O—P(O,NRH)—O—, —CH₂—P(O)₂—O—, —O—P(O)₂—CH₂—, and —O—Si(R")₂—O—; among which —CH₂—CO—NRH—, —CH₂—NRH—O—, —S—CH₂—O—, —O—P(O)₂—O—O—P(—O,S)—O—, —O—P(S)₂—O—, —NRHP(O)₂—O—, —O—P(O,NRH)—O—, —O—PO(R")—O—, —O—PO(CH₃)—O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[(CH₂)ₙO]ₘCH₃, O(CH2)ₙOCH₃, O(CH₂)ₙNH₂, O(CH₂)ₙCH₃, O(CH₂)ₙONH₂, and O(CH₂)ₙON[(CH₂)ₙCH₃]₂, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH₃, OCN, Cl, Br, CN, CF₃, OCF₃, SOCH₃, SO₂CH₃, ONO₂, NO₂, N₃, NH₂, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH₂CH₂OCH₃, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH₂)₂ON(CH₃)₂ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH₂—O—CH₂—N(CH₃)₂.

Still other modifications include 2'-methoxy (2'-O—CH₃), 2'-aminopropoxy (2'-OCH₂CH₂CH₂NH₂), 2'-allyl (2'-CH₂—CH=CH₂), 2'-O-allyl (2'-O—CH₂—CH=CH₂) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH₂—)n group bridging the 2' oxygen atom and the 4' carbon atom wherein n is 1 or 2. LNAs and preparation thereof are described in WO 98/39352 and WO 99/14226, the disclosures of which are incorporated herein by reference.

Chimerics

It is not necessary for all positions in a given compound to be uniformly modified, and in fact more than one of the aforementioned modifications may be incorporated in a single compound or even at a single nucleoside within an oligonucleotide. These "chimeric" antisense compounds typically contain at least one region including a modification as described herein, while the remainder of the oligonucleotide remains "unmodified."

In certain aspects, the modification confers increased resistance to nuclease degradation, increased cellular uptake, increased stability and/or increased binding affinity for the target nucleic acid. In other aspects the modification serves as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds may be formed as composite structures of two or more oligonucleotides, modified oligonucleotides, oligonucleosides and/or oligonucleotide mimetics as described above. Such compounds have also been referred to in the art as hybrids or gapmers. See, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, the disclosures of which are incorporated herein by reference in their entireties.

EXAMPLES

Example 1

Preparation of RNase-free Nanoparticles

Figure 2:
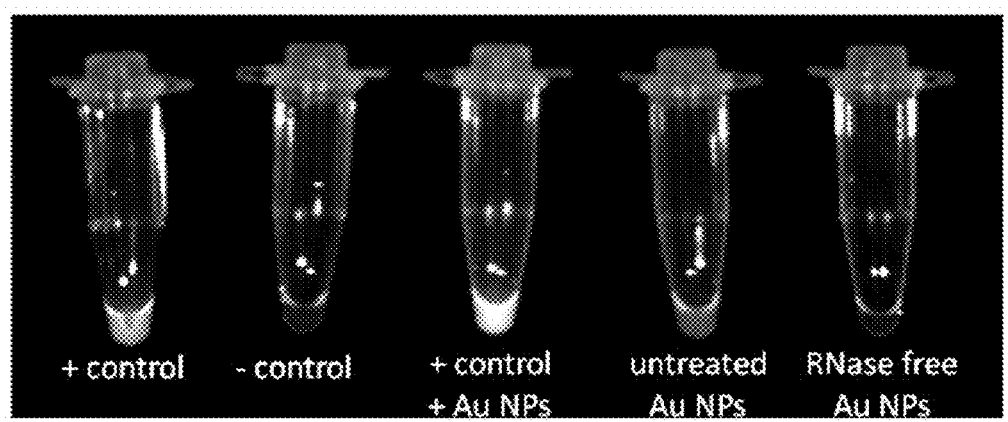
FIG. 2 depicts the presence of RNases in solutions of gold nanoparticles. Untreated Au NPs show a positive signal, while particles treated to eliminate RNase activity are rendered RNase free.

Citrate-stabilized gold nanoparticles (13 nm) were prepared using published procedures [Frens, Nature Physical Science 241: 20-22 (1973)]. Following synthesis, particles were treated with 0.1% diethylpyrocarbonate (DEPC) for 12 hours with stirring, then autoclaved at 121° C. for 60 minutes. Importantly and quite surprisingly, the optical and physical properties of the nanoparticles are unaffected by this relatively extreme treatment, as measured by UV spectroscopy and transmission electron microscopy TEM analysis (FIG. 1). Subsequent ligand functionalization also was not affected by this treatment. Testing of RNase activity in these solutions using an RNaseAlert kit (Ambion) showed no detectable RNase activity as compared to controls or untreated particles (FIG. 2).

Example 2

Modification of RNase-free Nanoparticles

The resultant RNase-free nanoparticles were amenable to further modification by thiolated oligonucleotides using published procedures [Demers et al., Anal. Chem. 72: 5535 (2000)]. Without this pre-treatment, subsequent functionalization with RNA could not be accomplished, presumably due to rapid degradation of the RNA-based surface capping ligands. Duplexes composed of a 27-base RNA strand, and 25-base complement terminated with an ethylene glycol spacer and alkylthiol, were hybridized and added to the RNase free Au NPs, where they were allowed to chemisorb via the thiol-gold bond. For this work, the sequences were designed to target the firefly luciferase gene.

RNA oligonucleotides were synthesized using TOM-RNA reagents (Glen Research) and a MerMade 6 (Bioautomation) or commercially made (Integrated DNA Technologies). The oligonucleotides synthesized by non-commercial sources were purified using TOP-RNA cartridges (Varian). The sequences used for this study were: luciferase sense, 5'-Phosphate rCrGrA rCrUrU rCrGrU rGrCrC rArGrA rGrUrC rUrUrU rCrGAC Spacer 18 Spacer 18-Thiol-3' (SEQ ID NO: 1), luciferase antisense, 5'-rGrUrC rGrArA rArGrA rCrUrC rUrGrG rCrArC rGrArA rGrUrC rGrUrA-3' (SEQ ID NO: 2), Cy3 luciferase, 5'-Cy3 rGrUrC rGrArA rArGrA rCrUrC rUrGrG rCrArC rGrArA rGrUrC rGrUrA-3' (SEQ ID NO: 3), Cy5 luciferase, 5'-Cy5 rGrUrC rGrArA rArGrA rCrUrC rUrGrG rCrArC rGrArA rGrUrC rGrUrA-3' (SEQ ID NO: 4), luciferase dabcyl, 5'-rCrGrA rCrUrU rCrGrU rGrCrC rArGrA rGrUrC rUrUrU rCrGrA C-dabcyl-3' (SEQ ID NO: 5), Renilla luciferase sense, 5'-Phosphate rGrGrA rGrGrA rCrGrC rUrCrC rArGrAr UrGrA rArArU rGrGGT Spacer 18 Spacer 18-Thiol-3' (SEQ ID NO: 6), Renilla luciferase antisense, 5' rArCrC rCrArU rUrUrC rArUrC rUrGrG rArGrC rGrUrC rCrUrG-3' (SEQ ID NO: 7).

Figure 3:
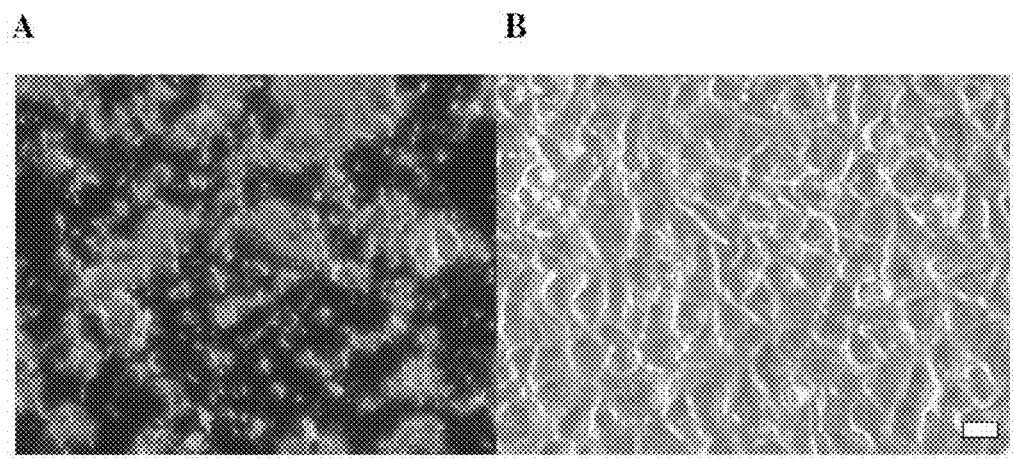
FIG. 3 depicts light microscopy images of confluent HeLa cells. In the synthesis of RNA nanoparticle compositions, 30 μmol/mL of oligoethylene glycol-thiol (OEG-thiol) was added as a surface passivating ligand following RNA duplex addition. This addition was found to prevent particle precipitation in culture. (a) RNA-nanoparticle compositions in cell culture without OEG-thiol addition show particle precipitation (black). (b) RNA-nanoparticle compositions in cell culture with OEG-thiol. Scale bar is 30 μm.

Pre-formed, thiolated RNA duplexes (1000 nM) were incubated with RNase-free solution of Au NPs (10 nM) which had been adjusted with 0.1 M NaCl. The mixture was aged in solutions of increasing salt concentration (from 0.1 to 0.3 M NaCl) and sonicated to increase the coverage of oligoribonucleotides on the surface. Oligoethylene glycol (OEG) was added (30 μmol/mL final concentration) 24 hrs after duplex addition and prevented particle precipitation in cell culture (FIG. 3). Addition at this concentration did not change duplex loading. After functionalization, the particles were purified by centrifugation at (13,000 rpm, 20 mins) at 4° C., and resuspended in sterile phosphate buffered saline (PBS: 137 mM NaCl, 10 mM Phosphate, 2.7 mM KCl, pH 7.4). This process was repeated three times. Refrigerated centrifugation was necessary to prevent duplex dehybridization due to heating caused by the centrifugation process. To determine dsRNA loading, antisense strands were labeled with Cyanine 3 (Cy3) fluorescent dye. Fluorescence was measured using a Jobin Yvon Fluorolog FL3-22 with excitation at 550 nm and measuring emission from 560 to 620 nm in 1 nm increments and compared to a standard curve. The number of duplexes per particle was calculated by oxidizing the gold using 25 μM potassium cyanide, measuring the number of fluorescent antisense strands (indicative of formed duplexes), and dividing by the concentration of nanoparticles. Each RNA-gold nanoparticle composition contained 33±4 RNA duplexes per 13 nm Au NP.

To prevent dehybridization of the RNA duplex, the salt concentration of the Au NP solution was adjusted to 0.1 M with NaCl prior to duplex addition. Subsequently, the salt concentration was increased from 0.1 to 0.3 M NaCl over 12 hours with brief ultrasonication following each addition to increase the coverage of oligonucleotides on the nanoparticle surface [Hurst et al., Anal Chem 78: 8313 (2006)]. To yield a more stable composition, RNA-functionalized particles were treated with 30 μmol/mL of oligoethylene glycol-thiol (OEG-Thiol) as an additional surface passivating ligand (Scheme 1). OEG-Thiol passivation was found to stabilize these nanomaterials under cell culture conditions for extended periods of time.

Scheme 1.
Preparation of Polyvalent RNA Gold Nanoparticle Compositions. RNA duplexes (containing a double-stranded RNA sequence, an ethylene glycol spacer, and an alkylthiol group) are formed via hybridizaiton and subsequently incubated with RNase free nanoparticles. Further passivation with oligoethylene glycol-thiol (OEG-Thiol) adds additional stability in cell culture.

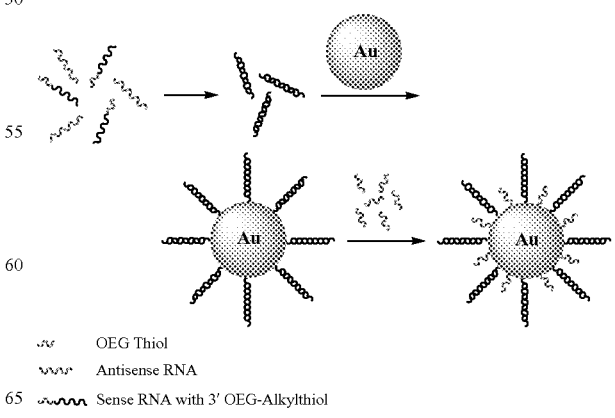

OEG Thiol
Antisense RNA
Sense RNA with 3' OEG-Alkylthiol

Example 3

Cellular Uptake of RNA-Nanoparticle Compositions

Figure 4:
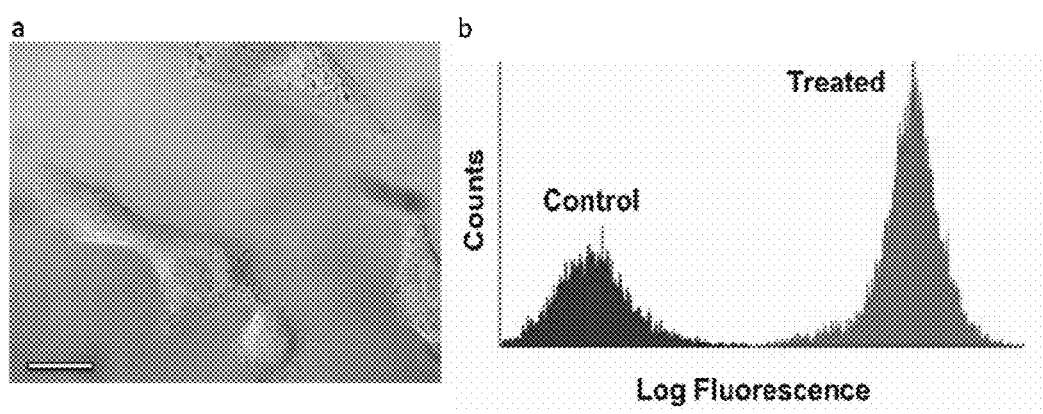
FIG. 4 depicts cellular uptake of RNA-Au NPs. (a) Fluorescence microscopy images of HeLa cells incubated for 6 hours with RNA-Au NPs (Cy5 labeled RNA). Scale bar is 20 μm (b) Flow cytometry analysis comparing RNA-Au NP treated cells to untreated controls.

The ability of the compositions to enter cells was investigated by confocal microscopy using fluorescent (Cyanine 5, Cy5) compositions prepared as above. RNA-Au NPs were added to cultures of HeLa cells. Cells were grown on glass coverslips and treated with nanoparticles functionalized with fluorophore-labled RNA duplexes. After 6 hours of treatment, the coverslips were removed, washed with PBS, and fixed to a chamber filled with PBS mounted on a glass slide. All images were obtained by scanning confocal microscopy (Zeiss 510 LSM) at 63× magnification and a 633 nm HeNe laser excitation source. Imaging studies reveal fluorescence throughout the cytoplasm of HeLa cells after 6 hours (FIG. 4a). It is interesting to note that like DNA Au-NPs, RNA Au-NPs require no transfection agent to enter cells [Giljohann et al., Nano Lett. 7: 3818 (2007)]. Indeed, analytical flow cytometry confirmed uptake of the RNA-Au NPs in >99% of the cell population (FIG. 4b). For the flow cytometry experiments, cells were treated with fluorescently-labeled (Cy5) RNA-nanoparticle compositions. Six hours post-transfection, cells were trypsinized to remove them from cell culture wells. Flow cytometry was performed using a DakoCytomation CyAn with excitation at 635 nm.

Example 4

Activity of RNA-Nanoparticle Compositions

Having determined that RNA-Au NPs are internalized by cells, the intracellular activity of RNA-gold nanoparticle compositions was examined next. Protein knockdown studies were performed in HeLa cells using a transfected luciferase plasmid as a target for this model system. HeLa cells (ATCC) were grown in Eagle's minimal essential medium (EMEM), with 10% heat-inactivated fetal bovine serum (FBS) and maintained at 37° C. in 5% $CO_2$. Cells were seeded in 96 well plates and grown for 1 day prior to transfection of a plasmid (psiCHECK 2, Promega) which contains both firefly luciferase and Renilla genes. Plasmid (0.2 µg per well) was added using Lipofectamine 2000 (Invitrogen) according to the manufacturer's recommendations. After plasmid introduction (24 hrs) the media was replaced with reduced serum media containing the functionalized RNA-Au NPs (3 nM nanoparticle concentration, ≈100 nM RNA duplex concentration) directed against firefly luciferase. On day one of treatment, the cells were approximately 70% confluent. At the conclusion of experiments, replicate wells of treated cells were counted and measured for viability using a Guava EasyCyte Mini (Guava Technologies). Viability after incubation was >98% for cells treated with RNA Au NPs.

For comparison, the same number of luciferase RNA duplexes (100 nM) were transfected using the commercial agent Lipofectamine 2000 according to the manufacturer's recommended protocol. After 24 hours of treatment, the media was replaced with fresh EMEM. Cells were assayed for luciferase expression using a Dual-Glo (Promega) assay according to the manufacturer's protocols after the indicated number of days.

Figure 5:
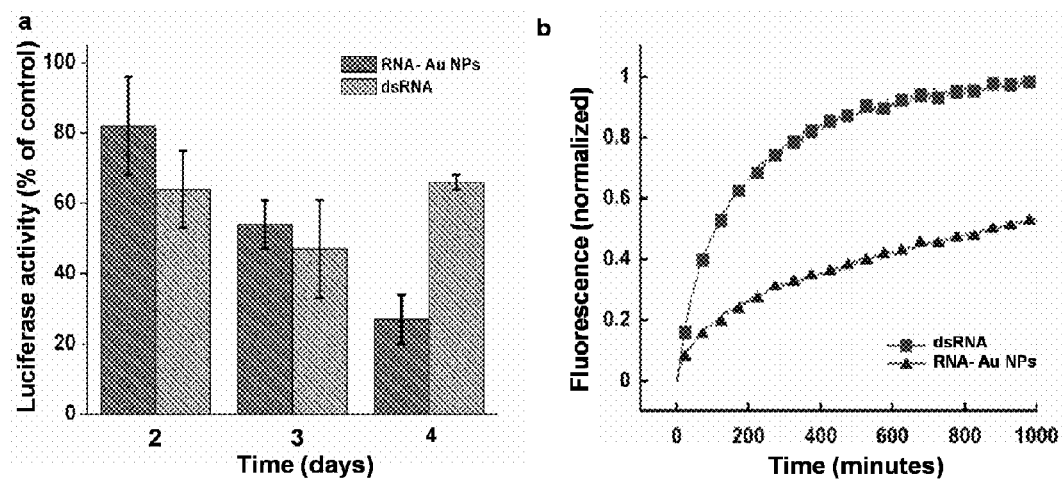
FIG. 5 depicts (a) Knockdown of luciferase expression over 4 days. (b) Stability of RNA-Au NPs. Comparison of the stability of dsRNA (squares) and RNA-Au NPs (triangles) in 10% serum.

Quantification of luciferase expression was normalized to controls that had not been transfected and revealed that the nanoparticle agents down-regulate firefly luciferase in a dose and time dependent manner. Control (Renilla) expression is not affected by RNA-Au NPs designed against firefly luciferase, indicating that the knockdown is also sequence specific. Interestingly, the results of three independent experiments with the RNA-Au NPs show knockdown that exceeds that of the free RNA four days after treatment (73±7% RNA-Au NPs vs. 33±2% free, FIG. 5a).

The persistent knockdown of luciferase is the result of the stabilization of the RNA on the nanoparticle. To make this determination, Cy3-labeled RNA particles were diluted to a concentration of 5 nM in 90 µL of PBS in a 96-well plate. For the dabcyl-labeled molecular RNA, the concentration was 150 nM. The microplate was placed into a Photon Technology International FluoDia T70 fluorescence plate reader that was maintained at 37° C. After allowing the sample to equilibrate (10 minutes), 10 µL of fetal bovine serum (FBS, Gemini Bioproducts) was added to bring the samples to 10% serum concentration. To prevent evaporation, the reaction was covered with 40 µL of mineral oil. The fluorescence of the sample (excitation=530 nm, emission=570 nm) was measured every 5 minutes for 48 hours. The base line fluorescence was determined from a sample treated with a 10 µL aliquot of PBS in place of FBS. The endpoint of the reaction was determined when no further increase in fluorescence as a function of time was observed. All samples were measured in triplicate.

In these stability experiments, compositions incubated in serum showed greatly enhanced stability relative to their molecular RNA counterparts. For example, in the presence of 10% serum, RNA-Au NP compositions had a 6-times greater half-life than molecular RNA duplexes (816±59 mins vs. 133±30 mins, FIG. 5b). These data indicate that nanoparticle conjugation provides significant protection from degradation in an extracellular context. Since the extracellular lifetime of RNA is of great importance for their storage, handling, and potential therapeutic application, nanoparticle conjugation may provide a significant advantage for the protection and delivery of functional RNA ligands. Importantly, this enhanced stability does not require chemical modifications to protect the integrity of the RNA.

Example 5

Orientation of Polynucleotide on Nanoparticle Surface

The orientation of RNA immobilized on a nanoparticle can be controlled. The strategy of immobilizing the RNA substrates for Dicer enzymes allows for the control of access to the dupex. Different immobilization chemistries, monothiol or dithiol, and different lengths of spacer sequences may be utilized to vary the number of and the distance between the RNA duplexes thus controlling the rates of RNA degradation.

Experiments were performed to determine whether Dicer, an RNase responsible for initiating RNAi in this system, would be able to recognize and cleave these duplexes. In a typical enzyme kinetic experiment, RNA-Au NPs (approximately 5 nM) were mixed with Dicer (0.1 U/mL final) in reaction buffer at 37° C. The rate of degradation of RNA duplex was measured by monitoring the fluorescence increase every 72 seconds for at least 12 hours. To determine minimum and maximum fluorescence, samples containing no enzyme (minimum) or 3 mM potassium cyanide (KCN) to dissolve the gold (maximum) were used. The KCN oxidizes the gold nanoparticles, eliminating the quenching of the fluorophore-labeled strands.

The number of duplexes per nanoparticle was determined by fluorescently labeling one or both of the strands and comparing the fluorescence associated with a given concentration of RNA-functionalized nanoparticles with a standard curve generated using the same strands. Results from a representative loading study are shown in Table 1.

TABLE 1

Determination of RNA duplex loading using two different RNA lading strategies. The conjugates contain fluorescein, either on the antisense strand (hybridized to the sense strand which is covalently linked to the nanoparticle), or in the case of the hairpin system, RNA is labeled with fluorescein on the 5' end.

| Type of nanoparticle composition | Location of fluorophore | Number of duplexes |
|---|---|---|
| Two strands | 5' end of the hybridized strand | 91 |
| Single strand RNA Hairpin | 5' end of the hairpin | 34 |

Figure 6:
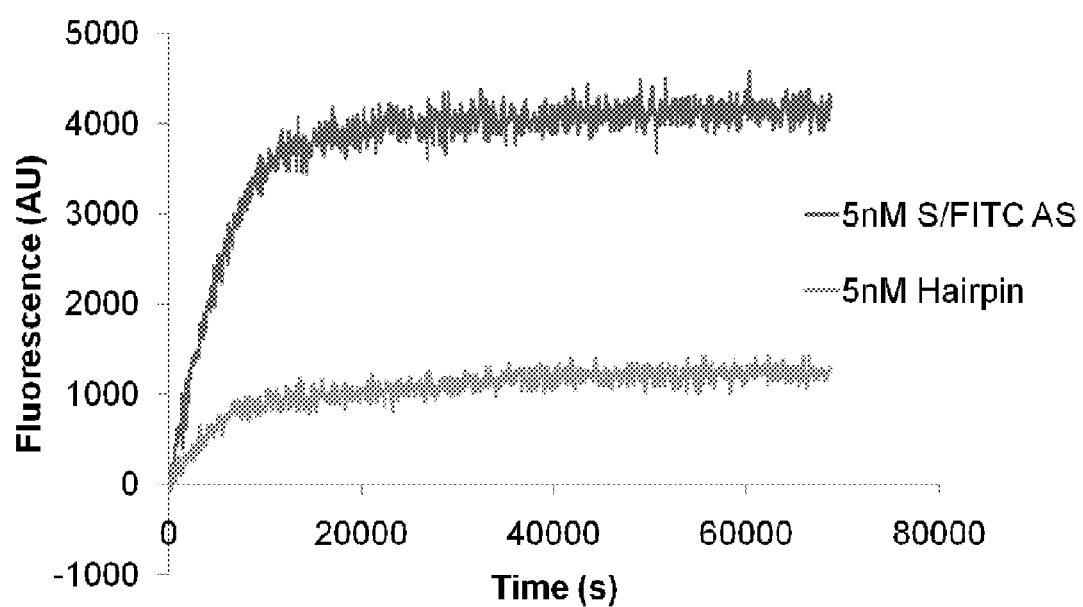
FIG. 6 depicts the activity of RNase III against RNA-Au NPs functionalized with two strands or a single strand hairpin RNA. Both systems are recognized by RNase III as substrates. The difference in maximum fluorescence is partially due to difference in loading (see table 1). Reaction with no added enzyme was used for background correction.

RNase III, a ribonuclease that is known to degrade dsRNAs, was compared to the activity of Dicer. Both RNase III and Dicer are active against the two systems tested as measured by increase in fluorescence above background (no enzyme added to reaction) over time. FIG. 6 shows the activity in the presence of RNase III.

Figure 7:
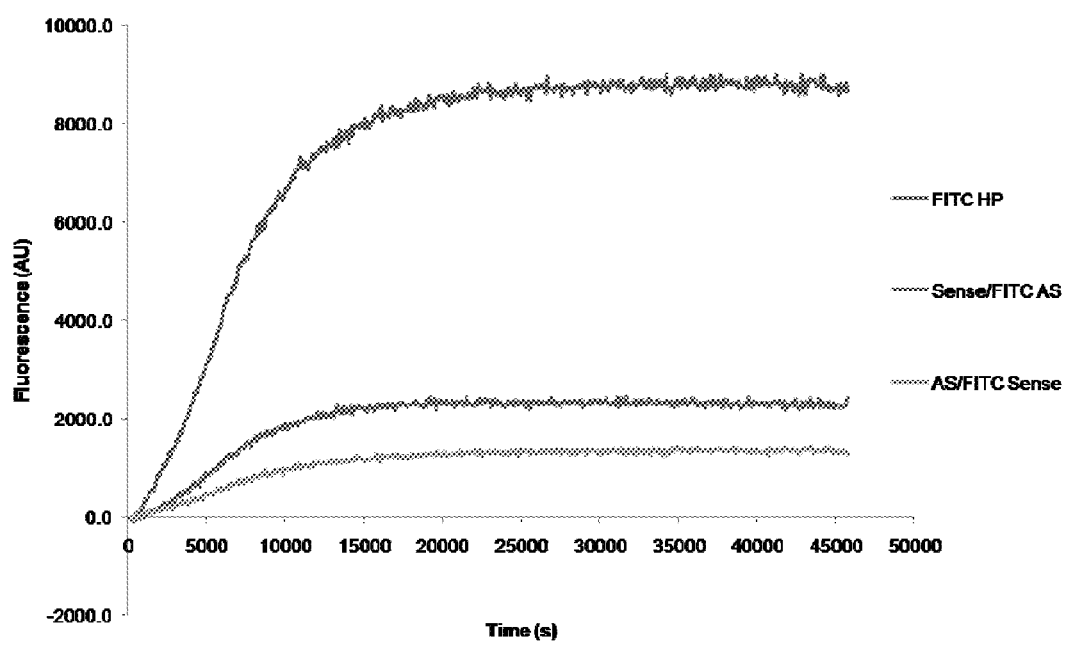
FIG. 7 depicts the activity of Dicer against RNA-Au NPs functionalized with two strands (Sense/FITC AS, AS/FITC Sense) or a single strand hairpin RNA (FITC HP). Both systems are recognized by Dicer as substrates, however higher activity can be seen in the case of sense strand immobilization. Difference in maximum fluorescence is partially due to difference in loading (see table 1). Reaction with no added enzyme was used for background correction.
Figure 8:
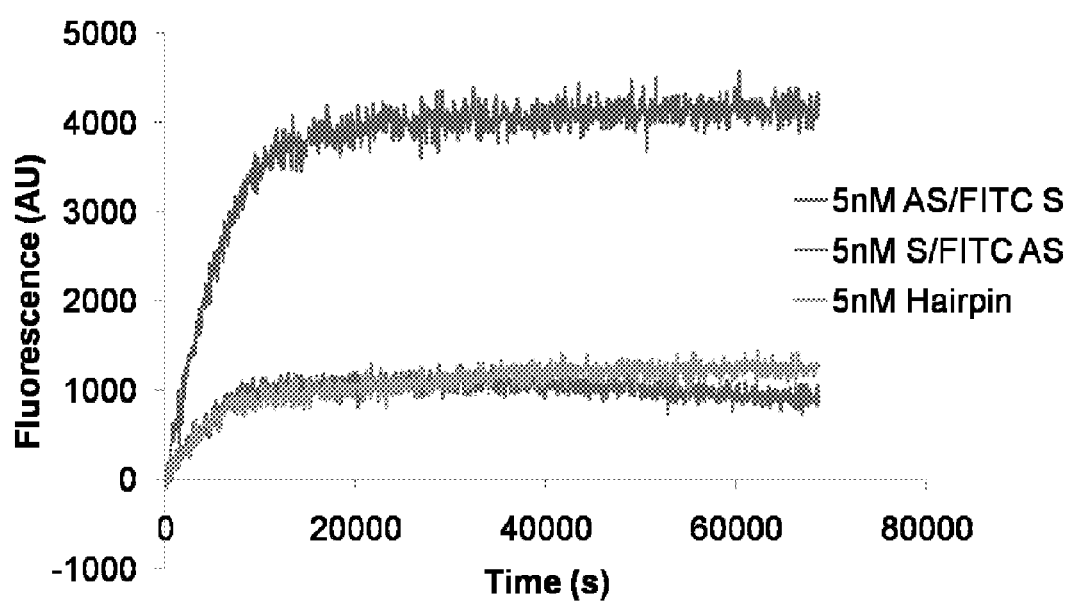
FIG. 8 depicts the activity of RNase III against immobilized sense, antisense, and hairpin RNA-Au NPs. For this enzyme, higher activity can be seen in the case where the sense strand is immobilized.

When each system was treated with Dicer in a similar manner to RNase III, a commensurate increase in fluorescence was observed over time (FIG. 7). Additionally, the absolute difference in fluorescence above background was higher for Dicer compared to RNase III. These data suggest that these RNAs are more specifically recognized by Dicer than by a nonspecific enzyme like RNase III when densely immobilized on the nanoparticle surface. Furthermore, preferences in orientation can be observed for the immobilization of the sense versus antisense strand (FIG. 8). In the case where the sense strand is chemically attached to the particle, higher activity is observed. Without being bound by theory, this may reflect the ability of the antisense strand to act as the guide strand in the RNAi machinery. This difference is contemplated to be of use in modulating and tuning the RNAi response in cells.

What is claimed is:

1. A nanoparticle composition comprising a duplex, the duplex comprising:
   (a) a ribonucleic acid (RNA) polynucleotide functionalized to the nanoparticle and comprising a sequence that is identical to a target polynucleotide; and
   (b) an additional polynucleotide having a sequence that forms the duplex with the RNA polynucleotide under conditions appropriate to form the duplex, the duplex providing a polypeptide interaction site;
   the additional polynucleotide having at least one domain sufficiently complementary to a sequence in the target polynucleotide to permit hybridization of the additional polynucleotide to the target polynucleotide under appropriate conditions; wherein
   the duplex is located distal and not proximal to the nanoparticle, and the distance of the duplex from the nanoparticle is equivalent to at least 10 nucleotides.

2. The nanoparticle composition of claim 1 wherein the RNA polynucleotide is covalently associated with the nanoparticle.

3. The nanoparticle composition of claim 1 wherein the RNA polynucleotide is not in covalent association with the nanoparticle.

4. The nanoparticle composition of claim 1 wherein the nanoparticle comprises at least two RNA polynucleotides, each RNA polynucleotide in association with the nanoparticle has an identical sequence.

5. The nanoparticle composition of claim 1 wherein the nanoparticle comprises at least two RNA polynucleotides and at least two RNA polynucleotides in association with the nanoparticle have different sequences.

6. The nanoparticle composition of claim 1, wherein the additional polynucleotide is RNA.

7. The nanoparticle composition of claim 1, wherein the additional polynucleotide is deoxyribonucleic acid (DNA).

8. The nanoparticle composition of claim 1 having surface density of the RNA of at least about 2 pmol/cm$^2$ to about 1000 pmol/cm$^2$.

9. The nanoparticle composition of claim 1 wherein the polypeptide interaction site associates with a protein selected from the group consisting of RNase H, RNase D, RNase L, RNase III, Dicer, Argonaute, Argonaute2, and human immunodeficiency virus transactivating response RNA-binding protein (TRBP).

10. The nanoparticle composition of claim 1 wherein the domain of the duplex is about 10 nucleotides in length.

11. The nanoparticle composition of claim 10 wherein the duplex further includes an additional domain sufficiently complementary to a second sequence in the target polynucleotide and hybridization of the additional domain of the duplex to the second sequence in the target polynucleotide creates an additional substrate site recognized by a second polypeptide.

12. The nanoparticle composition of claim 11, wherein the additional domain of the polynucleotide is about 10 nucleotides in length.

13. The nanoparticle composition of claim 11, wherein the substrate site and the additional substrate site are the same.

14. The nanoparticle composition of claim 11, wherein the substrate site and the additional substrate site are different.

15. The nanoparticle composition of claim 1, wherein the RNA polynucleotide is conjugated to the nanoparticle through a thiol linkage.

16. The nanoparticle composition of claim 1, wherein the RNA polynucleotide has a half-life that is at least a half-life of an identical RNA polynucleotide that is not associated with a nanoparticle.

17. The nanoparticle composition of claim 1, wherein the RNA polynucleotide has a half-life that is about 1-fold greater, about 2-fold greater, about 3-fold greater, about 4-fold greater, about 5-fold greater or more than a half-life of identical RNA that is not associated with a nanoparticle.

18. The nanoparticle composition of claim 1, wherein the RNA polynucleotide is about 5 to about 100 nucleotides in length.

19. The nanoparticle composition of claim 1, wherein the additional polynucleotide is about 5 to about 100 nucleotides in length.

20. The nanoparticle composition of claim 1 which is a gold nanoparticle.

21. The nanoparticle composition of claim 1 which is a silver nanoparticle.

22. A method of regulating expression of a target polynucleotide comprising the step of hybridizing the target polynucleotide with the domain of the nanoparticle composition of claim 1 to form a substrate site for a polypeptide.

23. The method of claim 22, wherein hybridizing results in degradation of the target polynucleotide.

24. The method of claim 22, wherein the polypeptide is selected from the group consisting of RNase H, RNase D, RNase L, RNase III, Dicer, Argonaute, Argonaute2, and TRBP.

* * * * *

SEQUENCE LISTING

```
<160> NUMBER OF SEQ ID NOS: 7

<210> SEQ ID NO 1
<211> LENGTH: 25
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Phosphate
<220> FEATURE:
<221> NAME/KEY: misc_structure
<222> LOCATION: (25)..(25)
<223> OTHER INFORMATION: 36 Carbon spacer bound to thiol group

<400> SEQUENCE: 1
cgacuucgug ccagagucuu ucgac                                         25

<210> SEQ ID NO 2
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 2
gucgaaagac ucuggcacga agucgua                                       27

<210> SEQ ID NO 3
<211> LENGTH: 27
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy3

<400> SEQUENCE: 3
gucgaaagac ucuggcacga agucgua                                       27

<210> SEQ ID NO 4
<211> LENGTH: 27
<212> TYPE: RNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy5

<400> SEQUENCE: 4
gucgaaagac ucuggcacga agucgua                                          27

<210> SEQ ID NO 5
<211> LENGTH: 25
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(25)
<223> OTHER INFORMATION: dabcyl

<400> SEQUENCE: 5
cgacuucgug ccagagucuu ucgac                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Phosphate
<220> FEATURE:
<221> NAME/KEY: misc_structure
<222> LOCATION: (25)..(25)
<223> OTHER INFORMATION: 36 Carbon spacer bound to thiol group

<400> SEQUENCE: 6
ggaggacgcu ccagaugaaa ugggt                                            25

<210> SEQ ID NO 7
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 7
acccauuuca ucuggagcgu ccug                                             24
```